(12) United States Patent
Takemoto et al.

(10) Patent No.: US 9,192,733 B2
(45) Date of Patent: Nov. 24, 2015

(54) PUNCTURE NEEDLE ASSEMBLY AND MEDICINAL LIQUID INJECTION DEVICE

(75) Inventors: Masafumi Takemoto, Yamanashi-ken (JP); Masashi Simizu, Yamanashi-ken (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 1094 days.

(21) Appl. No.: 13/255,573

(22) PCT Filed: Mar. 1, 2010

(86) PCT No.: PCT/JP2010/053259
§ 371 (c)(1),
(2), (4) Date: Oct. 3, 2011

(87) PCT Pub. No.: WO2010/103950
PCT Pub. Date: Sep. 16, 2010

(65) Prior Publication Data
US 2012/0010574 A1    Jan. 12, 2012

(30) Foreign Application Priority Data

Mar. 11, 2009   (JP) ................................. 2009-058791

(51) Int. Cl.
*A61M 5/00*    (2006.01)
*A61M 5/32*    (2006.01)

(52) U.S. Cl.
CPC ............... *A61M 5/326* (2013.01); *A61M 5/002* (2013.01); *A61M 2005/3247* (2013.01); *A61M 2005/3267* (2013.01)

(58) Field of Classification Search
CPC .................. A61M 2005/3267; A61M 5/3271; A61M 2005/3247; A61M 5/3202; A61M 5/326
USPC ................................. 604/110, 198, 263, 192
See application file for complete search history.

(56) References Cited

U.S. PATENT DOCUMENTS

| 4,894,055 A | 1/1990 | Sudnak |
| 2003/0014018 A1 | 1/2003 | Giambattista et al. |
| 2004/0193110 A1 | 9/2004 | Giambattista et al. |
| 2005/0277895 A1* | 12/2005 | Giambattista et al. ........ 604/198 |
| 2005/0283115 A1 | 12/2005 | Giambattista et al. |

FOREIGN PATENT DOCUMENTS

| JP | 2005-516691 A | 6/2005 |
| WO | WO 03/045481 A1 | 6/2003 |
| WO | WO 03/066141 A1 | 8/2003 |

OTHER PUBLICATIONS

International Search Report (PCT/ISA/210) issued on Mar. 30, 2010, by Japanese Patent Office as the International Searching Authority for International Application No. PCT/JP2010/053259.
Written Opinion (PCT/ISA/237) issued on Mar. 30, 2010, by Japanese Patent Office as the International Searching Authority for International Application No. PCT/JP2010/053259.

* cited by examiner

*Primary Examiner* — Bhisma Mehta
*Assistant Examiner* — Bradley Osinski
(74) *Attorney, Agent, or Firm* — Buchanan Ingersoll & Rooney PC

(57) ABSTRACT

A puncture needle assembly including: a puncture device which is provided with a needle tube having a sharp needlepoint at the tip thereof, and also with a protector which is supported relative to the needle tube so as to be movable in the axis direction of the needle tube between a first position at which the protector covers at least the needlepoint of the needle tube and a second position at which the protector exposes the needlepoint and is located further on the base end side than the first position; a cap which is removably mounted to the puncture device; a lock which can, when the protector is at the first position, maintain the position of the protector; and a lock release which, when the protector moves from the first position to the second position, enables the protector to move by releasing the locked state maintained by the lock. The cap has a prevention section which, in a cap-mounted state in which the cap is mounted on the puncture device with the protector located at the first position, prevents the lock from being unlocked.

14 Claims, 17 Drawing Sheets

PUNCTURE NEEDLE ASSEMBLY AND MEDICINAL LIQUID INJECTION DEVICE

TECHNICAL FIELD

The present invention relates to a puncture needle assembly and a medicinal liquid injection device provided therewith.

BACKGROUND ART

Prefilled syringes, each preliminarily filled with a medicinal liquid, have been known. Such a prefilled syringe includes an outer cylinder provided with a discharge port at the tip (distal end) thereof, a gasket inserted in the outer cylinder, and a plunger connected to the gasket, with a medicinal liquid contained in a space surrounded by the outer cylinder and the gasket.

Upon injecting a medicinal liquid into, for example, a living body by use of the prefilled syringe, a needle assembly having a hollow needle is mounted onto the discharge port of the outer cylinder, and the prefilled syringe is used in such a mounted state (see, for example, Patent Document 1). Further, in the mounted state, the inside of the outer cylinder and the inside of the hollow needle communicate with each other. The needle assembly described in Patent Document 1 includes a hollow needle, a tubular protector movable along the axial direction of the hollow needle between a first position, at which a hollow needle portion ranging to the needlepoint is covered, and a second position at which the needlepoint is exposed, a tubular support member externally supporting the protector in a movable manner, and a coil spring biasing the protector in a direction away from the second position and toward the first position. In the needle assembly described in Patent Document 1, during use of the needle assembly, when the protector is moved from the first position to the second position and then returned again to the first position, an engaging piece (resilient piece) provided on the support member protrudes toward the interior thereof, and comes into engagement with a base end surface (proximal surface) of the protector. This ensures that even if one attempts to move the protector further toward the second position, movement of the protector is restricted because the protector is in engagement with the engaging piece. Thus, the protector is inhibited from moving toward the side of the second position (see FIG. 4 of Patent Document 1).

However, the needle assembly described in Patent Document 1 has the following problem. For example, before use (in an unused state) thereof, if the needle assembly is dropped by mistake, the impact upon dropping may cause the protector to move from the first position to the second position and then return again to the first position. In this case as well, as mentioned above, movement of the protector is restricted by the engaging piece of the support member. Therefore, even though the needle assembly has not yet been used, the protector located at the first position cannot be moved to the second position, so that the needlepoint cannot protrude from the protector. In other words, the needle assembly cannot be put to use.

Patent Document 1: U.S. Pat. No. 4,894,055

SUMMARY OF THE INVENTION

It is an object of the present invention to provide a puncture needle assembly and a medicinal liquid injection device, such that when a protector located at a first position is inadvertently moved to a second position and then returned again to the first position, a lock means can securely be prevented from operating.

In order to attain the above object, according to the present invention, there is provided a puncture needle assembly including:

a puncture device, which is provided with a needle tube having a sharp needlepoint at a distal end thereof, and a protector, which is supported relative to the needle tube so as to be movable in an axial direction of the needle tube between a first position, at which the protector covers at least the needlepoint of the needle tube, and a second position, at which the protector exposes the needlepoint and is located on a proximal side relative to the first position;

a cap removably mounted on the puncture device;

lock means which, when the protector is at the first position, is capable of maintaining the position of the protector; and lock release means which, when the protector moves from the first position to the second position, enables the protector to move by releasing a locked state maintained by the lock means, wherein the cap has a prevention section which, in a cap-mounted state in which the cap is mounted on the puncture device with the protector located at the first position, prevents the lock means from becoming unlocked.

In addition, in the puncture needle assembly according to the present invention, preferably, the lock release means is prevented from operating in the cap-mounted state, and the lock release means is permitted to operate in a cap-removed state.

Further, in the puncture needle assembly according to the present invention, preferably, a biasing means is provided, which biases the protector in a direction away from the second position and toward the first position;

wherein, when the protector is pushed to move from the first position to the second position against a biasing force of the biasing means and then pushing thereof is released, the protector is biased by the biasing force of the biasing means to move to the first position; and wherein, when the protector at the first position thereafter attempts to move toward the second position, the lock means operates to prevent movement of the protector toward the side of the second position.

In addition, in the puncture needle assembly according to the present invention, preferably, the puncture device has a main body section including a tubular body section in which a portion of the needle tube is inserted, a hub to which a proximal portion of the needle tube is fixed and which is disposed at a proximal portion of the tubular body section, and an elastically deformable section provided on the distal side relative to the proximal portion of the tubular body section;

the protector is supported on the main body section and has an engaging section capable of engaging with the elastically deformable section when the protector is located at the first position; and the lock means is composed of the elastically deformable section and the engaging section.

Further, in the puncture needle assembly according to the present invention, preferably, the lock release means is composed of an engagement preventing member which, when the protector moves from the first position toward the second position, comes into contact with the engaging section and thereby exhibits an engagement preventing function, by which the engaging section is permitted to pass by the elastically deformable section without coming into engagement with the elastically deformable section.

In addition, in the puncture needle assembly according to the present invention, preferably, the engagement preventing member is mounted removably on the protector;

the elastically deformable section is located on the outer peripheral side of the engagement preventing member in a state in which the engagement preventing member is mounted on the protector when the protector is located at the first position; and in the cap-mounted state, the prevention section pushes the elastically deformable section toward the engagement preventing member, so as to bring the elastically deformable section into close contact with an outer peripheral portion of the engagement preventing member, thereby preventing the engagement preventing member from passing by the elastically deformable section.

Further, in the puncture needle assembly according to the present invention, preferably, the engagement preventing member is mounted removably on the protector;

the main body section has a pushing piece, which is disposed on the outer peripheral side of the elastically deformable section and pushes the elastically deformable section, and the elastically deformable section is located on the outer peripheral side of the engagement preventing member in a state in which the engagement preventing member is mounted on the protector when the protector is located at the first position; and in the cap-mounted state, the preventing section pushes the elastically deformable section through the pushing piece and toward the engagement preventing member, so as to bring the elastically deformable section into close contact with an outer peripheral portion of the engagement preventing member, thereby preventing the engagement preventing member from passing by the elastically deformable section.

In addition, the puncture needle assembly according to the present invention preferably includes positioning means which, when the cap-mounted state is established, performs positioning such that the prevention section confronts the elastically deformable section.

Further, in the puncture needle assembly according to the present invention, preferably, the prevention section constitutes a part of an inner peripheral portion of the cap.

In addition, in the puncture needle assembly according to the present invention, preferably, the cap is tubular in shape; and the prevention section is composed of a rib formed to project on an inner peripheral portion of the cap.

In order to attain the above object, according to the present invention, there is provided a medicinal liquid injection device including the puncture needle assembly according to the present invention; and further including:

a vessel, which is prefilled with a medicinal liquid, on which the puncture device of the puncture needle assembly is mounted, and which communicates with the needle tube in the mounted state.

DESCRIPTION OF THE EMBODIMENTS

The puncture needle assembly and the medicinal liquid injection device according to the present invention will be described in detail below, based on preferred embodiments thereof shown in the accompanying drawings.

First Embodiment

Figure 1:
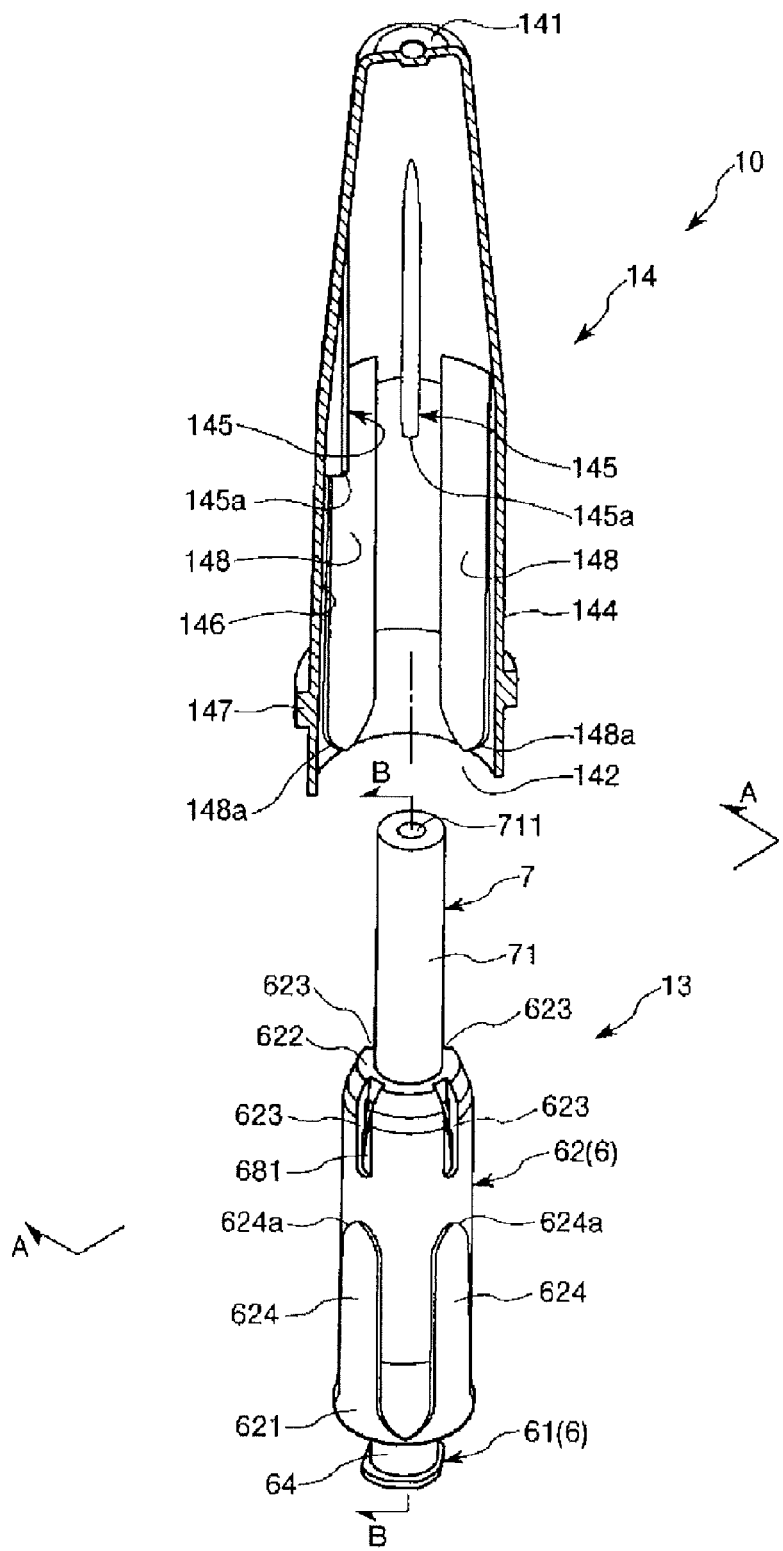
FIG. 1 is a perspective view showing a cap-removed state of a first embodiment of a puncture needle assembly according to the present invention.
Figure 2:
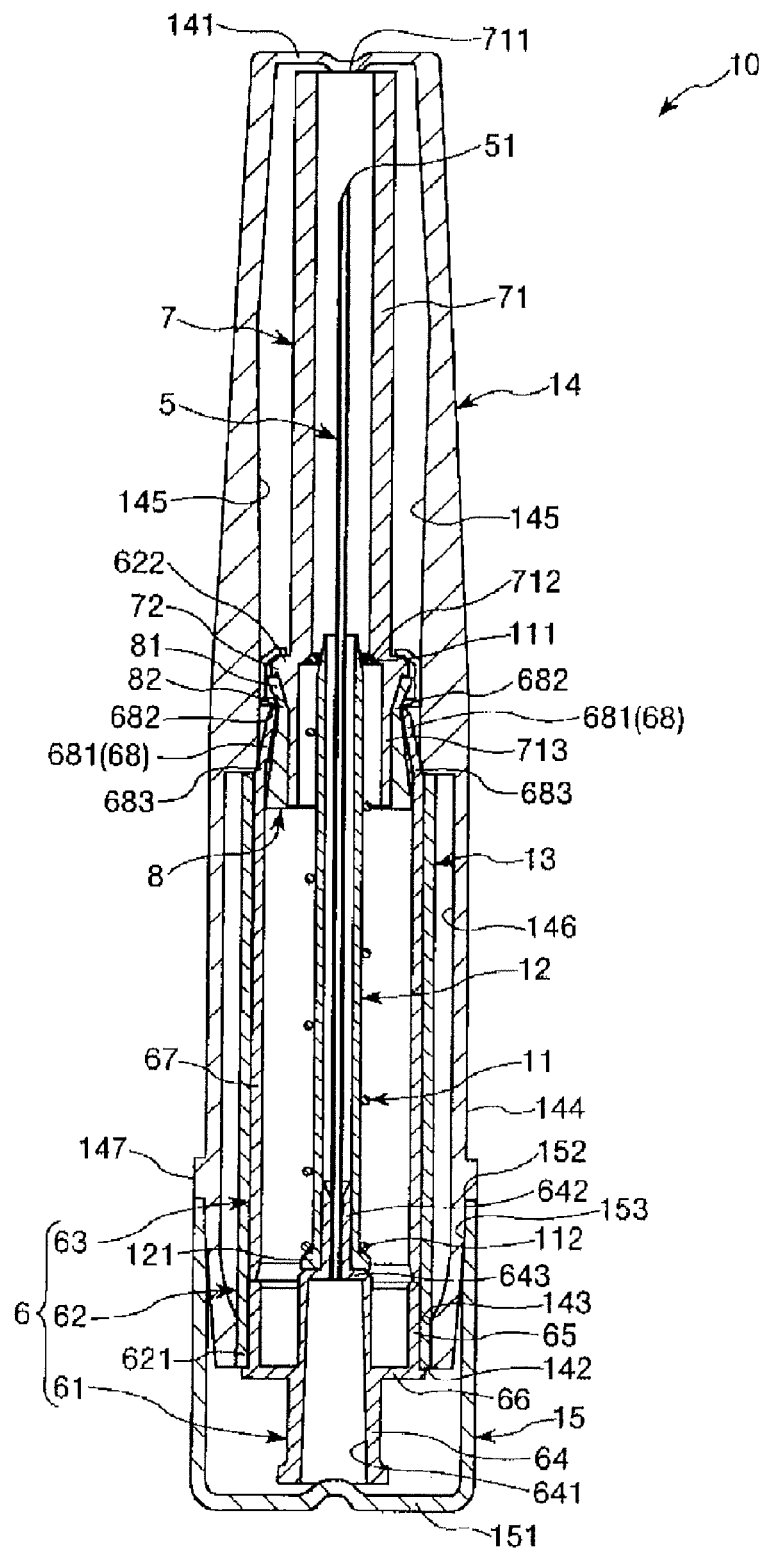
FIG. 2 is a longitudinal sectional view (a view corresponding to a section along line A-A of FIG. 1) showing a cap-mounted state of the puncture needle assembly according to the invention.
Figure 3:
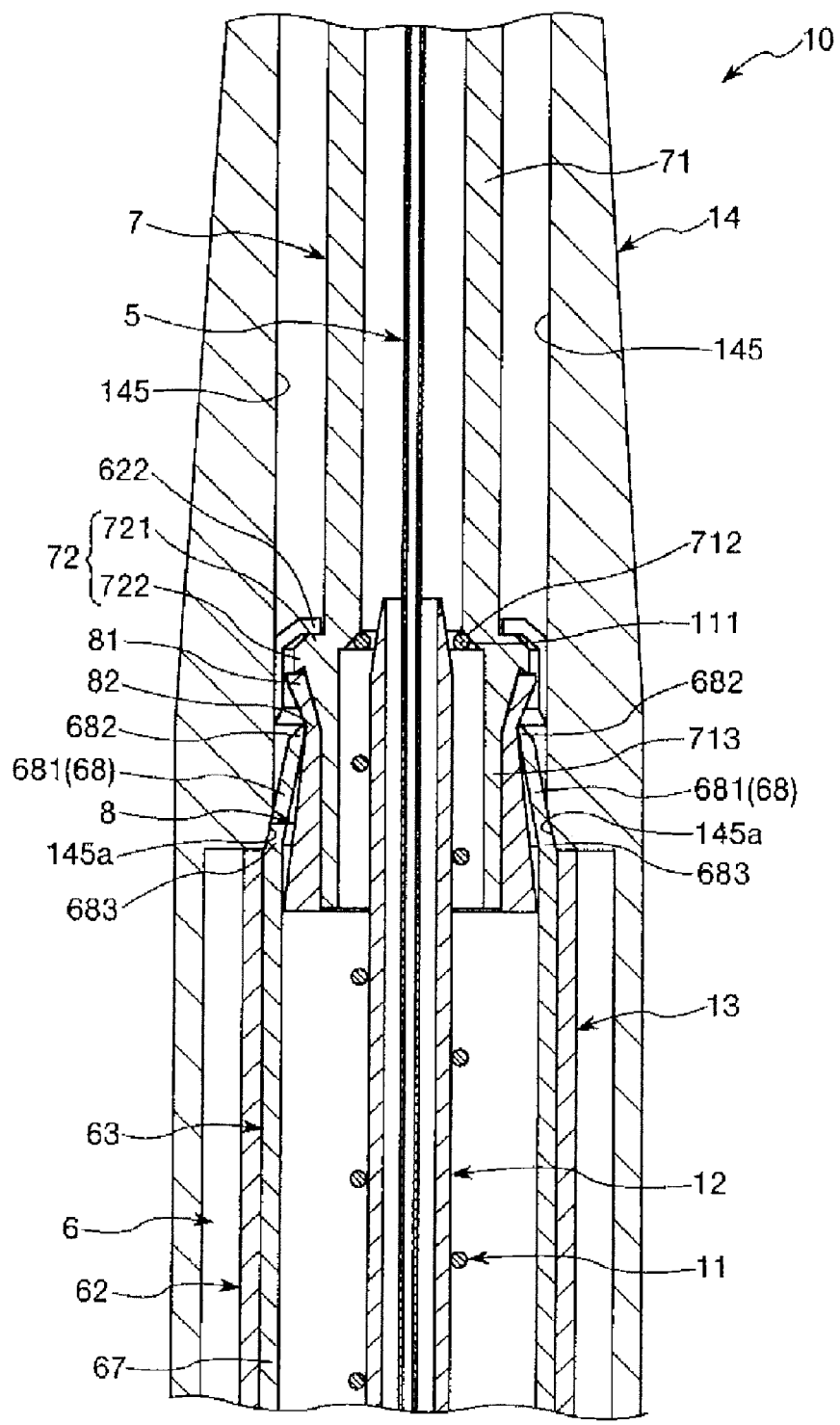
FIG. 3 is an enlarged longitudinal sectional view showing a major part of the puncture needle assembly shown in FIG. 2.
Figure 4:
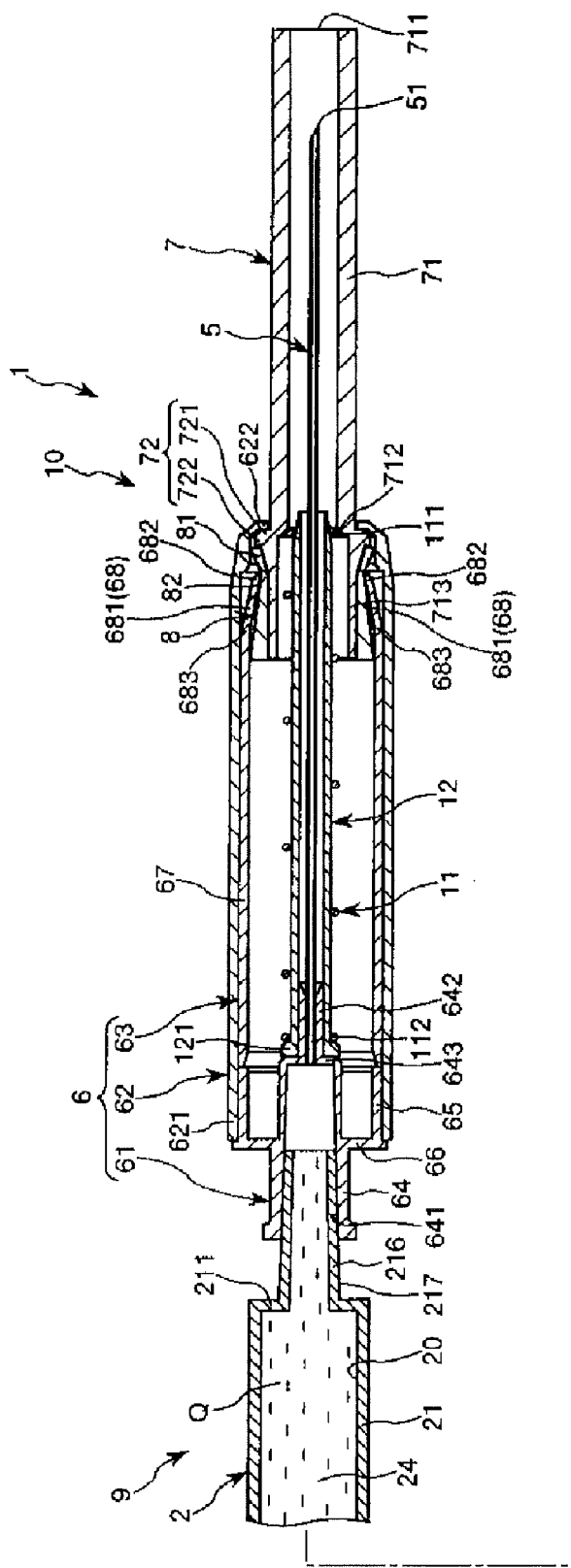
FIG. 4 is a longitudinal sectional view (a view corresponding to a section along line B-B of FIG. 1) for sequentially showing a state, during use of the first embodiment, of a medicinal liquid injection device (puncture needle assembly) according to the invention.
Figure 4:
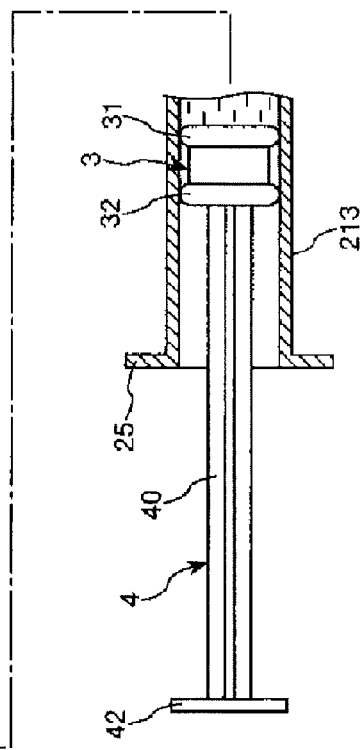
Figure 9:
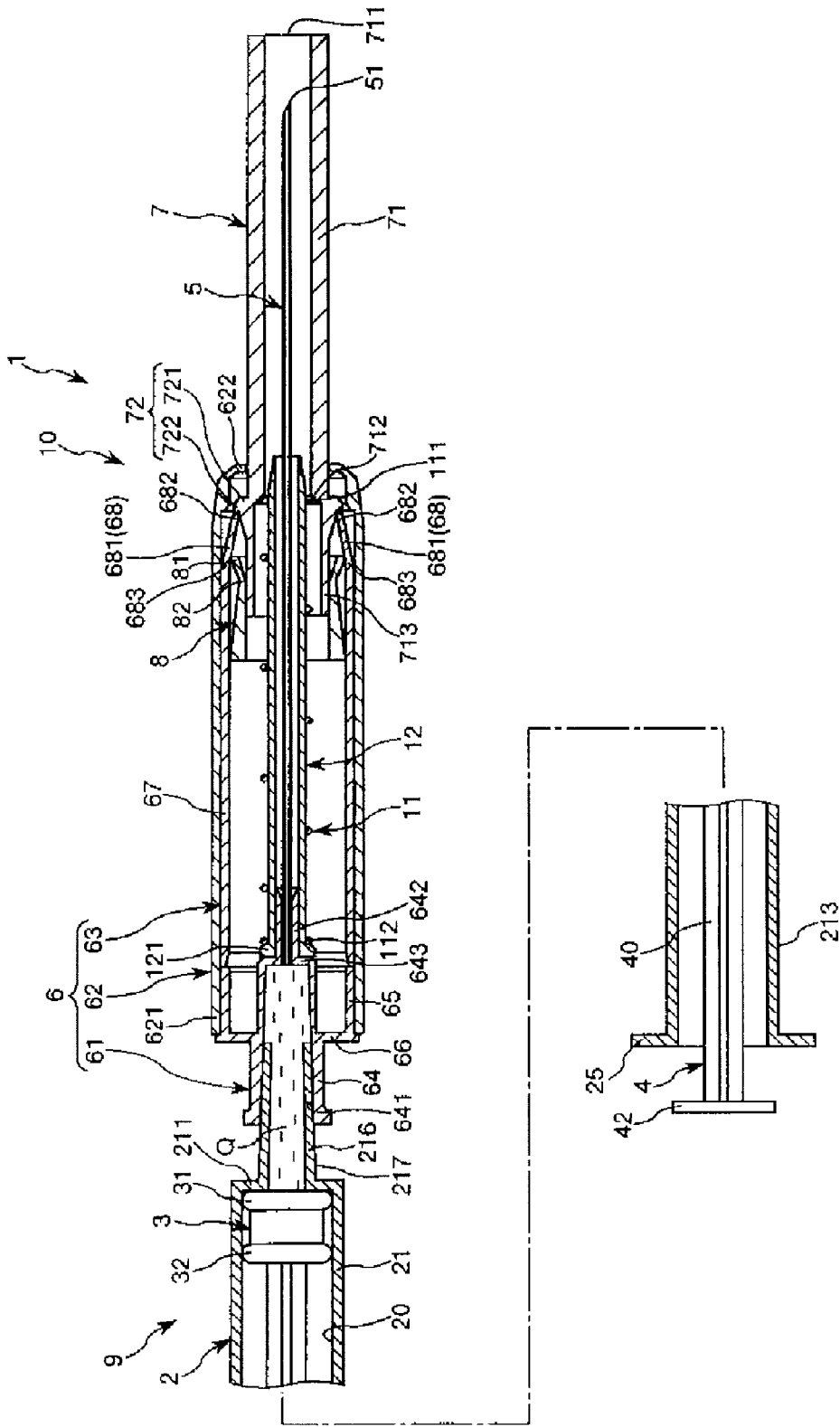
FIG. 9 is a longitudinal sectional view (a view corresponding to a section along line B-B of FIG. 1) showing a state, in a case where use of the medicinal liquid injection device shown in FIG. 4 is stopped midway.

FIG. 1 is a perspective view showing a cap-removed state of a first embodiment of the puncture needle assembly according to the present invention. FIG. 2 is a longitudinal sectional view (a view corresponding to a section along line A-A of FIG. 1) showing a cap-mounted state of the puncture needle assembly according to the present invention. FIG. 3 is an enlarged longitudinal sectional view showing a major part of the puncture needle assembly shown in FIG. 2. FIGS. 4 to 8 are respective longitudinal sectional views (views corresponding to a section along line B-B of FIG. 1) sequentially showing a state, during use of the first embodiment, of the medicinal liquid injection device (puncture needle assembly) according to the present invention. FIG. 9 is a longitudinal sectional view (a view corresponding to a section along line B-B of FIG. 1) showing a state, in a case where use of the medicinal liquid injection device shown in FIG. 4 is stopped midway. Incidentally, for the sake of convenience, in the following descriptions, the upper side in FIGS. 1 to 3 (as well as in FIGS. 15 to 17) is referred to as a "distal (side)," the lower side is referred to as a "proximal (side)," the right side in FIGS. 4 to 9 (as well as in FIGS. 10 to 14) is referred to as a "distal (side)," and the left side is referred to as a "proximal (side)."

The medicinal liquid injection device 1 shown in the respective drawings, which is a device to be used for injecting a medicinal liquid Q into a living body, is composed of a syringe 9 preliminarily filled with a medicinal liquid Q, and a puncture needle assembly 10 mounted on the syringe 9. Incidentally, the medicinal liquid Q that fills the syringe 9 of the medicinal liquid injection device 1 is appropriately selected according to the intended use thereof. Examples of medicinal liquids Q are those which are injected mainly through hypodermic injection and intramuscular injection, such as hematopoietic agents, vaccines, hormone preparations, antirheumatics, carcinostatic agents, anesthetics, anticoagulants, etc.

The configuration of each part will be described below.

The syringe 9 includes an outer cylinder 2, a gasket 3 slidable within the outer cylinder 2, and a plunger 4 connected to a proximal portion of the gasket 3.

The outer cylinder 2 has a mouth section 216 projecting in a distal direction from a bottom section 211 of an outer cylinder body 21, and is integrally formed with a plate-shaped flange 25 at the proximal end outer periphery (outer peripheral portion 213) thereof. A main body section 6 of the puncture needle assembly 10 is mounted onto the mouth section 216. In a state in which the puncture needle assembly 10 is mounted on the mouth section 216, the outer cylinder 2 and a needle tube (hollow needle) 5 of the puncture needle assembly 10 communicate with each other, so that when the plunger 4 is operated to move, the medicinal liquid Q flows through the mouth section 216 and into the needle tube 5 of the puncture needle assembly 10 (see FIG. 3).

The gasket 3, which is formed from an elastic material, is contained within the outer cylinder 2. On an outer peripheral portion of the gasket 3, two ring-shaped projections 31 and 32 are formed at a predetermined interval along the axial direction. The projections 31 and 32 are slid while maintained in close contact with an inner peripheral surface 20 of the outer cylinder 2, whereby liquid-tightness can be securely maintained, and enhanced sliding properties can be enabled. In addition, a space 24 that is surrounded by the gasket 3 and the outer cylinder 2 can be filled with the medicinal liquid Q.

The plunger 4 is connected to a proximal portion of the gasket 3. The plunger 4 operates the gasket 3 to move within the outer cylinder 2 along the axial direction thereof.

The plunger 4 principally includes a main body section 40, the cross section of which is composed of plate pieces arranged in a cross-shaped form. At the proximal end of the plunger 4, a flange-shaped finger rest section 42 is formed, which is integral with the main body section 40.

As shown in FIG. 2, the puncture needle assembly 10 includes a puncture device 13, a first cap 14 removably mounted on the puncture device 13, to be described later, and a second cap 15 removably mounted on the first cap 14.

The puncture device 13 includes the needle tube (hollow needle) 5, the main body section 6 having a hub (needle hub) 61 supporting the needle tube 5, a protector 7 capable of covering the needle tube 5 (needlepoint 51), a coil spring (biasing member) 11 serving as a biasing means for biasing the protector 7, and an engagement preventing member (lock release means) 8 contained within the main body section 6.

In addition, in an unused state of the puncture device 13, the protector 7 is contained within a space defined by the first cap 14 and the second cap 15, in a state of being located at a first position (see FIG. 2). Further, in this state, the first cap 14 is mounted on the distal side of the puncture device 13, and the second cap 15 is mounted on the proximal side of the first cap 14, which is thus mounted on the puncture device 13.

The needle tube 5 is formed with a sharp needlepoint 51 at a distal end thereof. The shape of the needlepoint 51 is not restricted. In the present embodiment, the needlepoint 51 is formed with a cutting edge surface, which is inclined at a predetermined angle against the axis of the needle tube 5.

The needle tube 5 may be formed, for example, from a metallic material such as stainless steel.

The main body section 6 has a hub 61, a tubular outside member 62 for connecting the hub 61 and the protector 7 to each other, and an inside member 63 contained inside the outside member 62.

The hub 61 is composed of a tubular inner cylinder section 64, a tubular outer cylinder section 65 provided on the outer peripheral side of the inner cylinder section 64, and a connecting section 66 for connecting the inner cylinder section 64 and the outer cylinder section 65 to each other.

The inner cylinder section 64 has a proximal portion into which the mouth section 216 of the syringe 9 is inserted. An inner peripheral portion 641 of the inner cylinder section 64 is tapered similarly to an outer peripheral portion 217 of the mouth section 216. Such a feature ensures that when the mouth section 216 of the syringe 9 is inserted into the inner cylinder section 64, the outer peripheral portion 217 of the mouth section 216 and the inner peripheral portion 641 of the inner cylinder section 64 are placed in close contact with each other. Accordingly, the puncture needle assembly 10 can be mounted (connected) to the syringe 9 in a liquid-tight manner.

A distal portion 642 of the inner cylinder section 64 is reduced in outside diameter and inside diameter. The inside diameter of the distal portion 642 is set to be equal to or slightly smaller than the outside diameter of the needle tube 5. Such a feature ensures that a proximal portion of the needle tube 5 is fitted onto the distal portion 642, whereby the needle tube 5 can be fixed.

The connecting section 66 is formed to project at an intermediate position of an outer peripheral portion of the inner cylinder section 64, and is flange-like in shape. The inner cylinder section 64 and the outer cylinder section 65 are connected to each other through the connecting section 66.

Incidentally, the hub 61 may include the inner cylinder section 64, the outer cylinder section 65 and the connecting section 66, which are integrally formed. Alternatively, such sections may be composed respectively of separate bodies, which are firmly connected to one another in order to constitute the hub 61.

The outside member 62 is tubular in shape. The outside member 62 is fixed to the hub 61 by fitting the proximal portion 621 thereof into the outer cylinder section 65 of the hub 61 from the outer peripheral side. Incidentally, the outside member 62 and the hub 61 may be fixed to each other, for example, by welding, adhesion or the like, or may be fixed jointly by means of such methods.

A projection 622 is formed at an inner peripheral portion of the distal end of the outside member 62, projecting toward the side (inside) of the needle tube 5 along the circumferential direction and over one entire circumference thereof. More specifically, the projection 622 has a ring-like shape with the center axis of the needle tube 5 serving as a center. The inside diameter of the projection 622 is set to be slightly greater than the outside diameter of a protector body 71 of the protector 7.

In addition, the outside member 62 is formed at the distal portion thereof with a plurality of (in the present embodiment, four) slits 623, which penetrate through the tube wall of the outside member 62. The slits 623 extend along the longitudinal direction of the outside member 62, and are arranged at regular intervals along the circumferential direction of the outside member 62.

The inside member 63 has a tubular section 67, which is tubular in the same manner as the outer cylinder section 65 of the hub 61, and an elastically deformable section 68, which is elastically deformable and provided at a distal portion of the tubular section 67.

The tubular section 67 forms a part for fixing the inside member 63 relative to the hub 61 and the outside member 62. Examples of fixing methods therefor may include fitting, welding, adhesion with an adhesive, etc., or combinations of such methods.

The tubular section 67 and the outside member 62 constitute a tubular body part of the main body section 6. The hub 61 is fixed to a proximal portion of the tubular body part. A portion that ranges from an intermediate portion to a proximal portion of the needle tube 5 (a part of the needle tube 5) is inserted into the tubular body part.

The elastically deformable section 68 is composed of a plurality of (in the present embodiment, two) small pieces 681 which project therefrom. The small pieces 681 are arranged intermittently around the axis of the needle tube 5. In the present embodiment, the small pieces 681 are arranged in an opposing manner to each other, with the needle tube 5 disposed therebetween. In other words, the small pieces 681 are arranged at regular interval(s). Incidentally, distal portions 682 of the small pieces 681 are located respectively on an inner side relative to the projection 622 of the outside member 62. In addition, each of the small pieces 681 is exposed through two of the four slits 623 (see FIG. 1).

Further, as shown in FIGS. 4 and 3, each of the small pieces 681 is disposed such that a surface on one side thereof is oriented toward the inner side (the needle tube 5 side), while the surface on the other side thereof is oriented toward the outer side (the side opposite to the needle tube 5). In addition, each of the small pieces 681 has a distal portion 682, which is inclined from a base portion 683 toward the axis of the needle tube 5.

Each of the small pieces 681 is elastically deformed outwardly when the distal portion 682 thereof is pressed from the inside toward the outside (in the vertical direction in FIGS. 1 and 2). When pressure is released in this manner, each of the small pieces 681 is restored elastically to its original shape.

As described later, when the protector 7 is in the first position and the puncture needle assembly 10 is in a cap-mounted or unused state, the elastically deformable section 68, which is composed of the small pieces 681, comes into contact with a presser rib (prevention section) 145 of the first cap 14, to be described later, whereby the small pieces 681 are securely prevented from opening toward the outside.

As mentioned above, the hub 61, the outside member 62, and the inside member 63 (the elastically deformable section 68), which constitute the main body section 6, are composed respectively of separate members. In the present embodiment, such members are firmly connected to one another. However, alternatively, such members may be composed of a single member.

Incidentally, the materials constituting the main body section 6, the protector 7 and the engagement preventing member 8, respectively, are not specifically restricted, and various plastic materials can be used.

Figure 6:
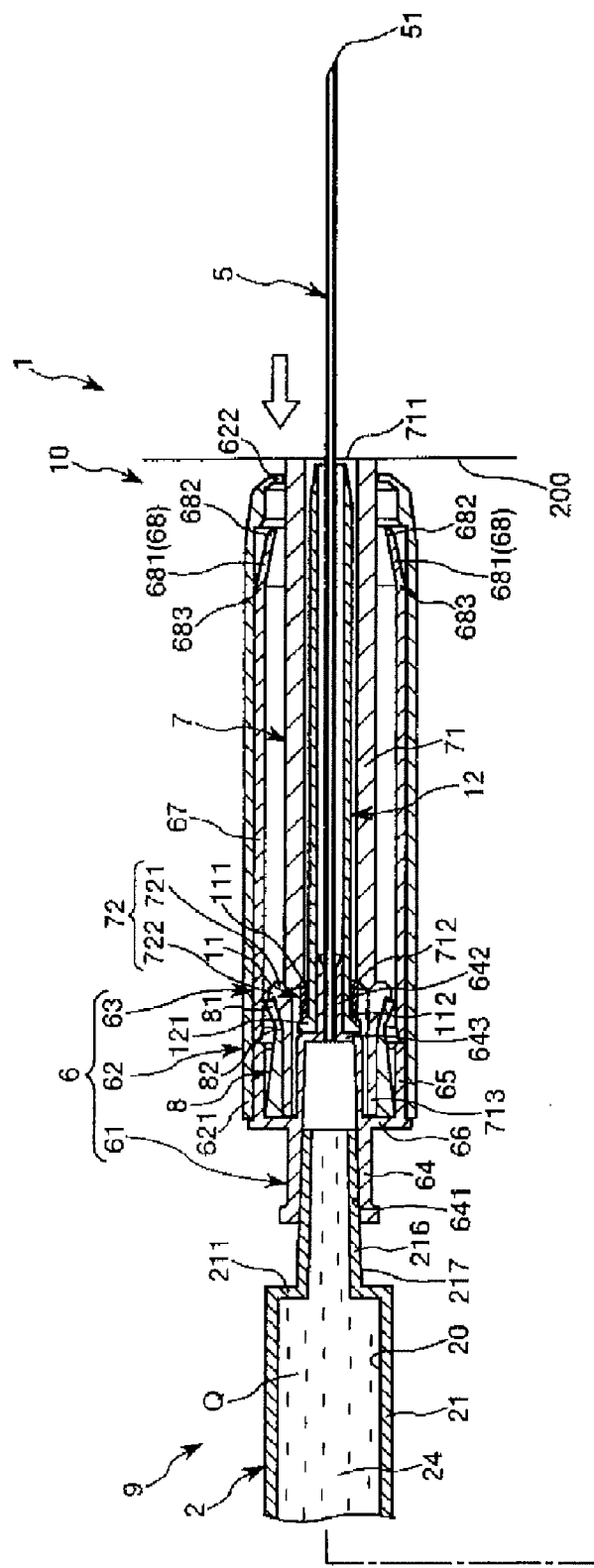
FIG. 6 is a longitudinal sectional view (a view corresponding to a section along line B-B of FIG. 1) for sequentially showing a state, during use of the first embodiment, of the medicinal liquid injection device (puncture needle assembly) according to the invention.
Figure 6:
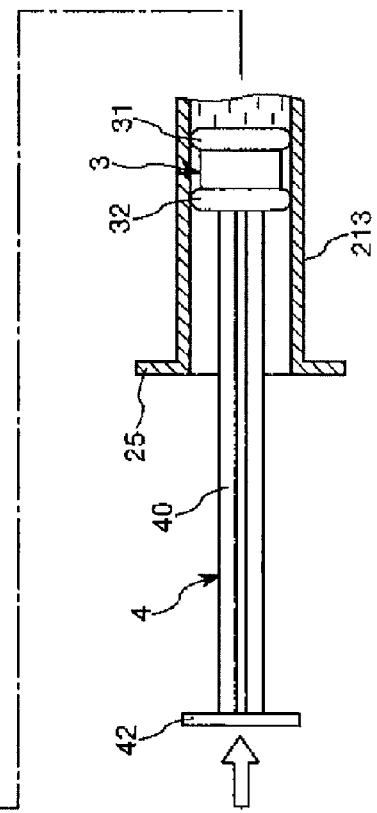

The protector 7 is supported by the main body section 6 so as to be movable along the axial direction of the needle tube 5. More specifically, the protector 7 can be moved along the axial direction of the needle tube 5 between a first position, as shown in FIGS. 1, 2, 4 and 7, at which the protector 7 covers the needlepoint 51 of the needle tube 5, and a second position, as shown in FIG. 6, at which the protector 7 is retracted from the first position in order to expose the needlepoint 51.

The protector 7 includes a tubular protector body 71, and a rib (projection) 72 provided at a proximal portion 713 of the protector body 71.

The protector body 71 is tubular in shape and opens at distal and proximal end portions thereof. As shown in FIG. 6, when the protector 7 is located at the second position, the needlepoint 51 protrudes from a distal opening 711 of the protector body 71. Such a feature makes it possible to puncture a living body surface (target part) 200 with the needlepoint 51. Further, when the plunger 4 is operated and pushed in this condition, the medicinal liquid Q can be administered into the living body.

The rib 72 is formed in a ring-like shape at an outer peripheral part of a proximal portion 713 of the protector body 71, along the circumferential direction and over the entire circumference thereof. The rib 72 is contained within the main body section 6, such that when the protector 7 is located at the first position, the rib 72 is located between the projection 622 of the outside member 62 and the small pieces 681. In addition, a portion on the distal side of the rib 72 constitutes a contact section 721, which contacts the projection 622 of the outside member 62, while a portion on the proximal side of the rib 72 constitutes an engagement section 722, which comes into engagement with the small pieces 681.

The outside diameter of the contact section 721 is set to be greater than the inside diameter of the projection 622 of the outside member 62. This enables the contact section 721 to come into contact with the projection 622 of the outside member 62 when the protector 7 is located at the first position (see FIGS. 1, 2 and 5). This also prevents the protector 7 from moving further (further from the first position) in the distal direction, whereby the protector 7 is prevented from becoming released (disengaged) from the main body section 6.

In addition, when the elastically deformable section 68 is in a natural state, the outside diameter of the rib 72 of the protector 7 is set to be greater than the spacing between distal portions 682 of the two small pieces 681. Such a feature enables the engagement section 722 to come into engagement with the small pieces 681. More specifically, when the protector 7 is moved from the first position to the second position and then returned to the first position, the rib 72 of the protector 7 engages with the small pieces 681 (see FIG. 6). As a result, the protector 7 is prevented from moving toward the side of the second position, and the protector 7 can be securely prevented from moving again toward the second position.

Accordingly, unintentional exposure of the needlepoint 51 of a used needle tube 5 from the protector 7 can securely be prevented.

Therefore, in the puncture needle assembly 10, the engagement section 722 of the protector 7 and the small pieces 681 of the main body section 6 function as a lock means, by which the state upon return of the protector 7 again to the first position can be maintained. Further, the lock means, which is brought about through engagement of the engagement section 722 of the protector 7 with the small pieces 681 of the main body section, prevents the protector 7 from moving toward the side of the second position, if the protector 7, having returned to the first position, attempts to move again toward the second position.

In addition, as mentioned above, the small pieces 681 are arranged intermittently about the axis of the needle tube 5. Therefore, the area of engagement (area of contact) between the small pieces 681 and the engagement section 722 can be made comparatively large, thereby assuring more reliable engagement between the engagement section 722 and the small pieces 681.

Further, the rib 72 functions to elastically deform the elastically deformable section 68, by pressing the elastically deformable section 68 outwardly when the protector 7 is moved from the second position toward the first position. Therefore, when the protector 7 is moved from the second position to the first position, the small pieces 681 are elastically deformed, and the rib 72 of the protector 7 is capable of passing by the small pieces 681.

Incidentally, it is not necessary for the rib 72 to be formed over one entire circumference, insofar as the rib 72 is formed at a position corresponding to the small pieces 681 of the protector body 71, i.e., at a position capable of engagement with the small pieces 681. For example, the rib 72 may be formed in a shape obtained by cutting out a portion of a ring-shaped part (annular part), e.g., a C-shape, or a plurality of rib pieces may be arranged intermittently.

In the interior of the inside member 63 of the main body section 6, an engagement preventing member (lock release means) 8 is mounted to the protector 7, so as to be movable along the axial direction of the needle tube 5. The engagement preventing member 8 exhibits an engagement preventing function, such that, when the protector 7 is moved from the first position toward the second position, the engagement preventing member 8 moves together with the protector 7 and comes into contact with the rib 72, thereby permitting the rib 72 to pass by (pass beyond) the elastically deformable section 68, without coming into engagement with the elastically deformable section 68. In other words, the engagement preventing member 8 functions to prevent the engagement section 722 from coming into engagement with the elastically deformable section 68, as well as elastically deforming the elastically deformable section 68, by moving together with the protector 7 when the protector 7 is moved from the first position toward the second position. This ensures that when the protector 7 is moved from the first position to the second position, the rib 72 of the protector 7 does not engage with the distal portions 682 of the small pieces 681, and is capable of passing over the distal portions 682 (see FIGS. 4 to 6). Thus, the engagement preventing member 8 can maintain the engaged state (locked state) between the rib 72 of the protector 7 and the small pieces 681 of the main body section 6 released, until the protector 7 moves from the first position to the second position.

The engagement preventing member 8 is tubular in shape, and is removably mounted on a proximal portion 713 of the protector body 71, i.e., on an outer peripheral portion on the proximal side of the rib 72 of the protector body 71 (such that the proximal portion 713 of the protector body 71 is inserted into the engagement preventing member 8).

In a state in which the engagement preventing member 8 is mounted on the proximal portion 713 of the protector body 71 (hereinafter referred to simply as a "mounted state"), a distal portion 81 of the engagement preventing member 8 and the rib 72 of the protector 7 are placed in contact with each other, or are capable of making contact with each other. This ensures that when the protector 7 is moved from the first position toward the second position, the engagement preventing member 8 is securely moved together with the protector 7, whereby the engagement preventing function can be exhibited.

In addition, when the protector 7 is located at the first position, i.e., in the mounted state, the elastically deformable section 68 is located on the outer peripheral side of the engagement preventing member 8, and the distal portions 682 of the small pieces 681 are located respectively at a contact section 82 (described later) of the engagement preventing member 8.

A distal portion 81 of the engagement preventing member 8 forms a part which, when the engagement preventing member 8 is moved from the first position to the second position together with the protector, comes into contact with the rib 72 to thereby prevent the rib 72 from engaging with the small pieces 681, and pushes the small pieces 681 outwardly causing elastic deformation thereof.

The outside diameter of the distal end of the engagement preventing member 8 is set so as not to be smaller than the outside diameter of the rib 72. This ensures that when the protector 7 is moved from the first position to the second position, the rib 72 is securely prevented from coming into engagement with the small pieces 681, and the small pieces 681 are elastically deformed so that the rib 72 can pass over the small pieces 681.

In addition, the engagement preventing member 8 includes the contact section 82, which makes contact with the distal portions 682 of the small pieces 681 in a natural state. The outside diameter of the engagement preventing member 8 increases gradually from the contact section 82 toward the distal portion 81 of the engagement preventing member 8. Such a structure, in which the outside diameter of the engagement preventing member 8 is increased gradually, ensures that when the protector 7 is moved from the first position to the second position, the small pieces 681 can smoothly be deformed elastically.

Further, the engagement preventing member 8 is configured such that when it is moved from the first position to the second position together with the protector 7, and thereafter the protector 7 is moved toward the first position, i.e., when the protector 7 is returned again to the first position, the engagement preventing member 8 becomes disengaged from the protector 7 (the proximal portion 713 of the protector body 71) and only the protector 7 is returned again to the first position. Consequently, as mentioned above, when the protector 7 is returned again to the first position, the rib 72 comes into engagement with the small pieces 681, whereby the protector 7 can securely be prevented from moving again toward the second position.

In addition, in a mounted state, a tiny gap is formed between an inner peripheral surface of the engagement preventing member 8 and an outer peripheral surface of the proximal portion 713 of the protector body 71. This ensures that, when the engagement preventing member 8 is disengaged from the protector 7, or in other words, when the protector 7 is moved from the second position to the first position, the engagement preventing member 8 can become disengaged smoothly and reliably.

Further, the outside diameters of the distal end and the proximal end of the engagement preventing member 8 are set respectively to be slightly smaller than the inside diameter of the tubular section 67. This ensures that the protector 7 is movably supported by the tubular section 67 through the engagement preventing member 8. On the other hand, as mentioned above, the inside diameter of the projection 622 of the outside member 62 is set to be slightly larger than the outside diameter of the protector body 71. This ensures that the protector 7 is movably supported by the projection 622 (the outside member 62). Therefore, the tubular section 67 and the projection 622 of the outside member 62 function together as a guide section for guiding the protector 7 when the protector 7 is moved from the first position toward the second position. This enables the protector 7 to be moved stably.

Incidentally, in the configuration shown in the drawings, in the mounted state, the position of the proximal end of the engagement preventing member 8 in the axial direction of the needle tube 5 and the position of the proximal end of the protector 7 coincide with each other. However, the invention is not limited thereby. One of the proximal end of the engagement preventing member 8 and the proximal end of the protector 7 may be located on the proximal side relative to the other.

A coil spring 11 is disposed between the main body section 6 and the protector 7. The coil spring 11 has a distal portion 111 in contact with a rear end stepped part 712 of the protector body 71. In addition, a proximal portion 112 of the coil spring 11 is in contact with a flange 121, which is formed on the outer periphery of the proximal end of a buckling preventive member 12, as will be described later.

With the coil spring 11 disposed in this way, the protector 7 can be securely biased by the coil spring 11 in the distal direction, or in a direction from the second position toward the first position.

Incidentally, the material constituting the coil spring 11 is not specifically restricted. For example, a metallic material such as stainless steel can be used.

In addition, the main body section 6 is provided therein with the buckling preventive member 12, which is inserted into and passed through the coil spring 11. The buckling preventive member 12 is tubular in shape, and a proximal portion thereof is fitted into a distal portion 642 of the inner cylinder section 64 of the hub 61. A flange 121 of the buckling preventive member 12 is in contact with a stepped part 643, which is formed on the proximal side and in the vicinity of the distal portion 642. The buckling preventive member 12 is a member that prevents buckling of the coil spring 11, by supporting the coil spring 11 from the inside at times when the coil spring 11 is contracted as a result of being pressed by the protector 7 that has been displaced to the second position (see FIG. 4).

As shown in FIGS. 1 and 2, the first cap 14 is tubular in shape, and has a distal closure section 141 formed by closing the distal end thereof. The puncture device 13 can be inserted into the first cap 14 via a proximal opening section 142. A proximal portion of the outside member 62 of the puncture device 13 is fitted into a fitting section (reduced-diameter section) 143, which is formed at an inner peripheral portion of the proximal end of the first cap 14, and which is reduced in inside diameter. This ensures that the first cap 14 is mounted properly on the puncture device 13.

In addition, the second cap 15 has a tubular shape, i.e., a bottomed tube-like shape, which has a proximal closure section 151 formed by closing the proximal end thereof. The puncture device 13, with the first cap 14 mounted thereon, can be inserted into the second cap 15 from a distal opening section 152 thereof. At a position where the distal opening section 152 of the second cap 15 comes into contact with a flange part (enlarged-diameter part) 147 at an outer peripheral portion of the first cap 14, a distal inner peripheral portion 153 of the second cap 15 is fitted onto an outer peripheral portion 144 of the first cap 14, whereby the second cap 15 is mounted. Hereinafter, this state will be referred to as a "cap-mounted state." On the other hand, when the puncture device 13 is used, the second cap 15 is disengaged therefrom, the puncture needle assembly 10 is mounted on the syringe 9, and thereafter, the first cap 14 is removed. Hereinafter, this state will be referred to as a "cap-removed state." In the cap-mounted state, as shown in FIG. 2, the space defined by the first cap 14 and the second cap 15 is placed in a gas-tight condition, so that sterility of the space and of the puncture device 13 contained within the space can be maintained.

The materials that constitute the first cap 14 and the second cap 15 are not specifically restricted. For example, the same or similar materials as those described above in relation to the outer cylinder 2 can be used. Further, the first cap 14 and the second cap 15 may be constituted from the same or different materials.

As shown in FIGS. 1 and 2, the first cap 14 is formed with a plurality of (in the present embodiment, four) presser ribs 145. The presser ribs 145 are formed to project on an inner peripheral portion 146 of the first cap 14, and extend at an intermediate portion along the longitudinal direction. Further, the presser ribs 145 are arranged at regular intervals along the circumferential direction of the inner peripheral portion 146 of the first cap 14. In addition, as shown in FIG. 3, the presser ribs 145 are formed with chamfered corner parts 145a at proximal portions thereof.

Operations of the medicinal liquid injection device 1 under a state of use thereof will be described below.

[1] First, the puncture needle assembly 10, in an unused state, and the syringe 9, which is prefilled with a medicinal liquid Q in a sufficient liquid amount for administration into a living body, are prepared. As shown in FIG. 2, in the unused state, the puncture device 13 of the puncture needle assembly 10 is contained within a space defined by the first cap 14 and the second cap 15. In addition, the protector 7, with the engagement preventing member 8 mounted on the proximal portion 713 thereof, is located at the first position.

In addition, when the puncture needle assembly 10 is in the unused state or in the cap-mounted state shown in FIG. 2, the puncture device 13 has the small pieces 681 of the main body section 6 in contact with the presser ribs 145 of the first cap 14, whereby the small pieces 681 are securely prevented from opening outwardly.

As shown in FIGS. 2 and 3, when the first cap 14 including the presser ribs 145 is in the cap-mounted state, the corner parts 145a of the presser ribs 145 are inserted respectively into the slits 623 in the main body section 6 of the puncture device 13, whereby the base portions 683 of the small pieces 681, which are exposed from the slits 623, are pressed toward the engagement preventing member 8 located on the inner side. As a result, the small pieces 681 are pressed inwardly, and the distal portions 682 thereof are placed in engagement with the contact section 82 of the engagement preventing member 8.

Thus, the distal portions 682 of the small pieces 681 are placed in engagement with the contact section 82 of the engagement preventing member 8. This ensures that, even when the puncture needle assembly 10 in the state shown in FIG. 2 is dropped by mistake, for example, a situation in which the protector 7, which is located at the aforementioned first position, might pass over (pass beyond) the small pieces 681 of the main body section 6 of the puncture device 13 together with the engagement preventing member 8, and due to the impact of being dropped, the aforementioned lock means is caused to move toward the second position, can be restrained (prevented) from occurring.

Then, the second cap 15 is removed, the puncture needle assembly 10 is mounted on the syringe 9, and thereafter, the first cap 14 is removed. As a result, the medicinal liquid injection device 1 is assembled, and a state is established in which the medicinal liquid injection device 1 can be used (see FIG. 4). Incidentally, at a time when the puncture needle assembly 10 is mounted on the syringe 9, the protector 7 is located at the first position, so that the needle tube 5 is covered at a portion ranging to the needlepoint 51 thereof. Accordingly, during the mounting process, accidental sticking with the needlepoint 51 can securely be prevented from occurring.

Figure 5:
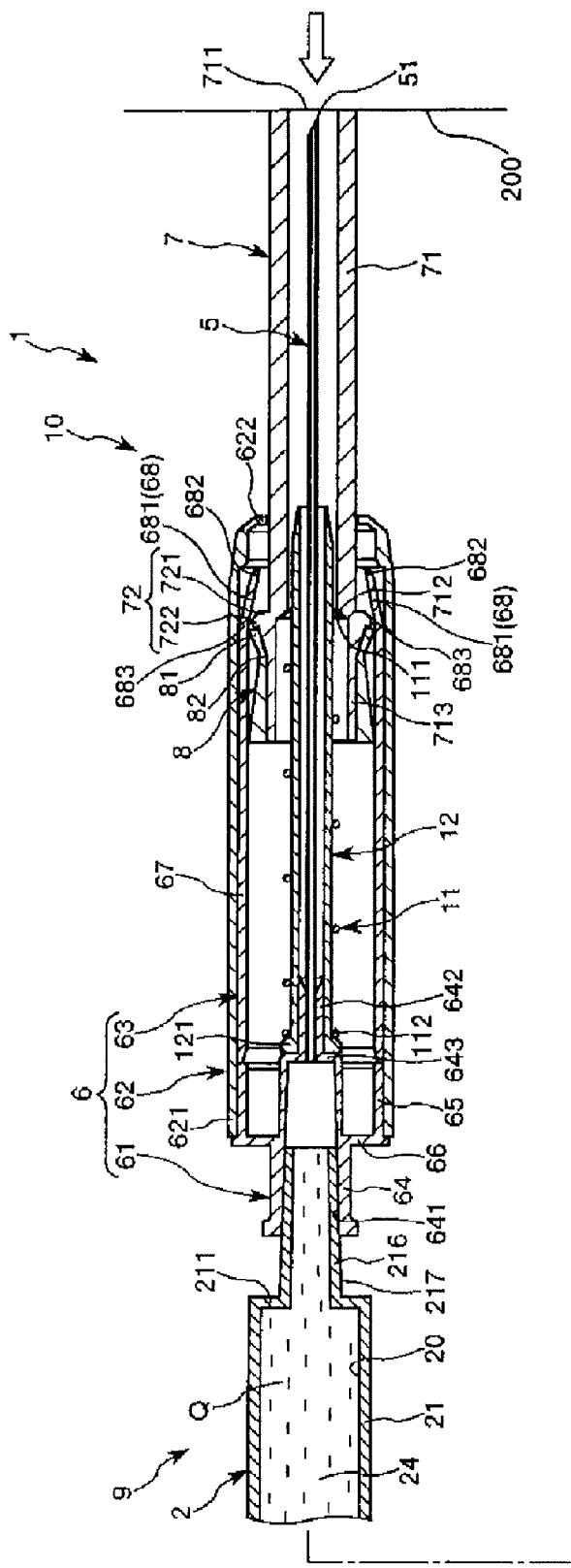
FIG. 5 is a longitudinal sectional view (a view corresponding to a section along line B-B of FIG. 1) for sequentially showing a state, during use of the first embodiment, of the medicinal liquid injection device (puncture needle assembly) according to the invention.
Figure 5:
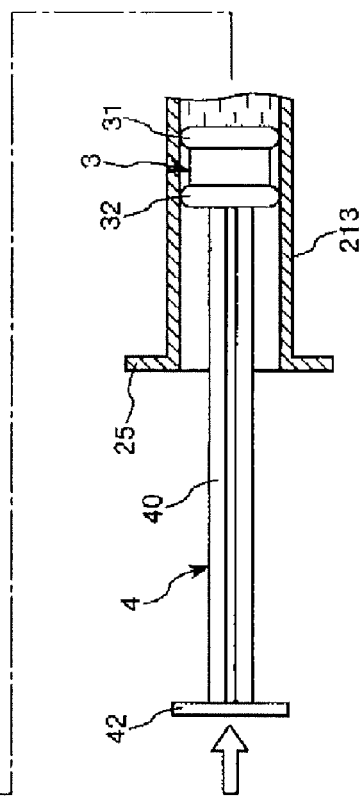

[2] Next, starting from the state shown in FIG. 4, the outer cylinder 2 is gripped, and the distal opening 711 of the protector 7 is pressed against a part to be punctured of a living body surface 200 against the biasing force of the coil spring 11, whereby the protector 7 is moved to the second position (see FIGS. 5 and 6). As a result, the needlepoint 51 of the needle tube 5, having been covered with the protector 7, protrudes in the distal direction via the distal opening 711 of the protector 7, to thereby puncture the living body surface 200 (see FIG. 6).

In addition, when the protector 7 and the engagement preventing member 8 are moved toward the second position, the distal portion 81 of the engagement preventing member 8 presses the distal portions 682 of the small pieces 681 of the inside member 63 outwardly while in contact with the rib 72 of the protector 7. As a result of such pressing, the small pieces 681 undergo elastic deformation as mentioned above, so that the distal portion 81 of the engagement preventing member 8 and the rib 72 of the protector 7 are capable of moving beyond the distal portions 682 of the small pieces 681, without becoming engaged with the distal portions 682. When the rib 72 moves beyond the small pieces 681, the pressure exerted on the small pieces 681 is released, so that the small pieces 681 are restored elastically to their original state.

Further, the movement of the protector 7 toward the second position is performed until the proximal end of the protector 7 and the proximal end of the engagement preventing member 8 come into contact with the connecting section 66 of the hub 61 (see FIG. 6). As a result, the fact that the protector 7 has been located assuredly in the second position, and therefore, that the needlepoint 51 can protrude from the protector 7, can be confirmed.

[3] Subsequently, while maintaining the state in which the living body surface 200 is punctured with the needlepoint 51 of the needle tube 5, the index finger and the middle finger, which grip the outer cylinder 2, are placed on an edge portion of the flange 25 of the outer cylinder 2, while the thumb is placed on the finger rest section 42 of the plunger 4. Then, the finger rest section 42 is pushed in the distal direction by the thumb (see FIG. 6). By this action, the gasket 3 is moved in the distal direction, and accordingly, the medicinal liquid Q in the space 24 inside the outer cylinder 2 is made to pass sequentially through the mouth section 216 of the outer cylinder 2, the inner cylinder section 64 of the main body section 6, and the needle tube 5, so as to be injected securely into the living body.

[4] After administration of the medicinal liquid Q, the medicinal liquid injection device 1 (the protector 7) is separated from the living body surface 200. In this instance, the pressure exerted on the protector 7 from the living body surface 200 is released, and the protector 7 is pressed in the distal direction by the restoring force (biasing force) of the coil spring 11, whereby the protector 7 moves toward and is returned to the first position (see FIG. 7). As a result, the needle tube 5 is covered again to the needlepoint 51 thereof. This ensures that accidents, such as scattering of blood that adheres to the needlepoint 51 or accidental sticking with the blood-contaminated needlepoint 51, can be prevented, so that infections caused by the blood can be prevented from occurring.

In addition, when the protector 7 is returned to the first position, the engagement preventing member 8 is released from the proximal portion 713 of the protector body 71 by the frictional force between the hub 61 and the outer cylinder section 65, so as to be left at the proximal portion of the main body section 6, and only the protector 7 is returned to the first position.

Further, when the protector 7 is returned to the first position, the rib 72 of the protector 7 presses the small pieces 681 of the inside member 63 outwardly. As a result of such pressing, the small pieces 681 undergo elastic deformation as mentioned above, so that the rib 72 of the protector 7 is capable of passing beyond the distal portions 682 of the small pieces 681. When the rib 72 passes beyond the small pieces 681, the pressure exerted on the small pieces 681 is released, and the small pieces 681 are restored elastically to their original state.

Figure 7:
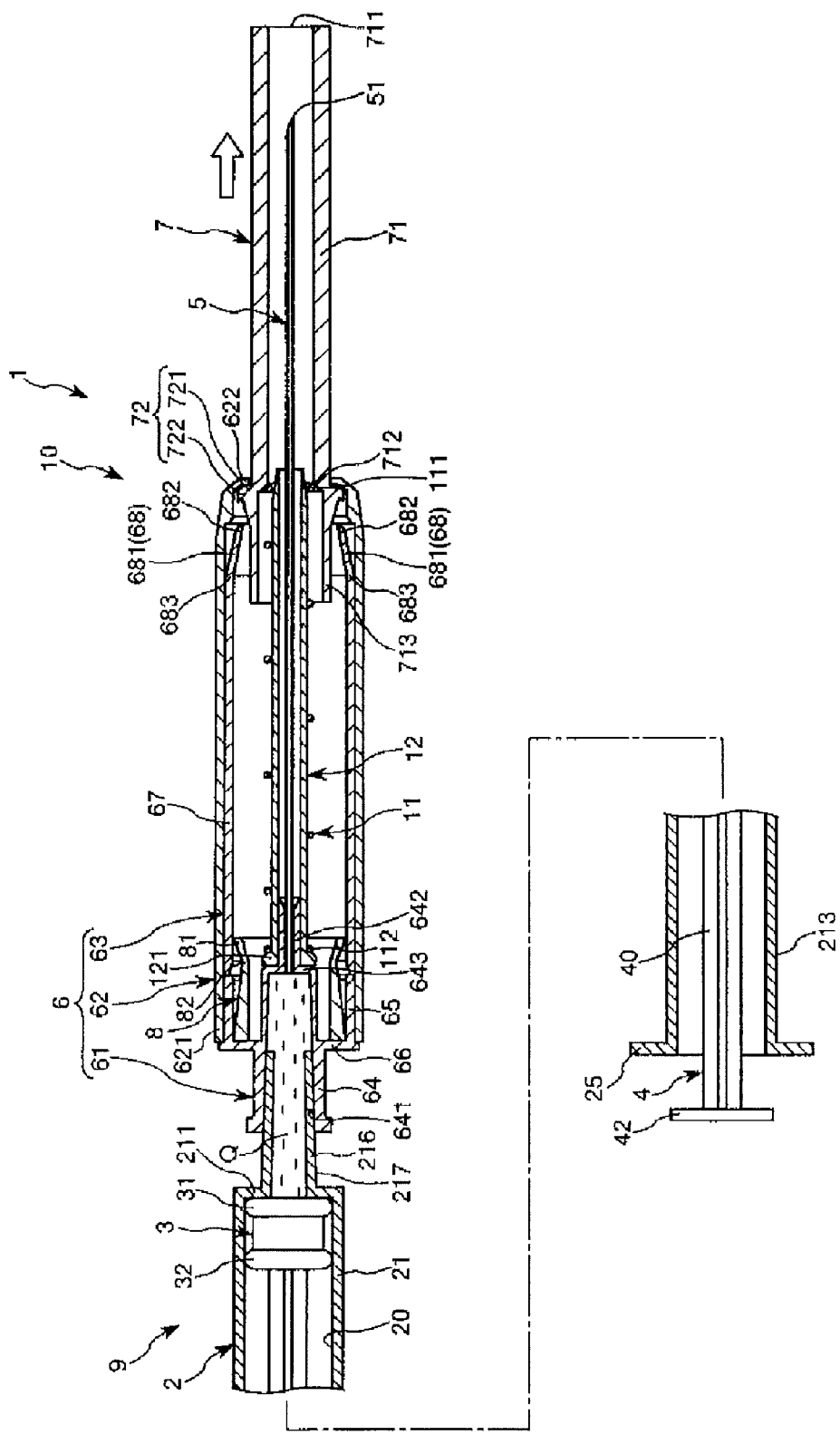
FIG. 7 is a longitudinal sectional view (a view corresponding to a section along line B-B of FIG. 1) for sequentially showing a state, during use of the first embodiment, of the medicinal liquid injection device (puncture needle assembly) according to the invention.
Figure 8:
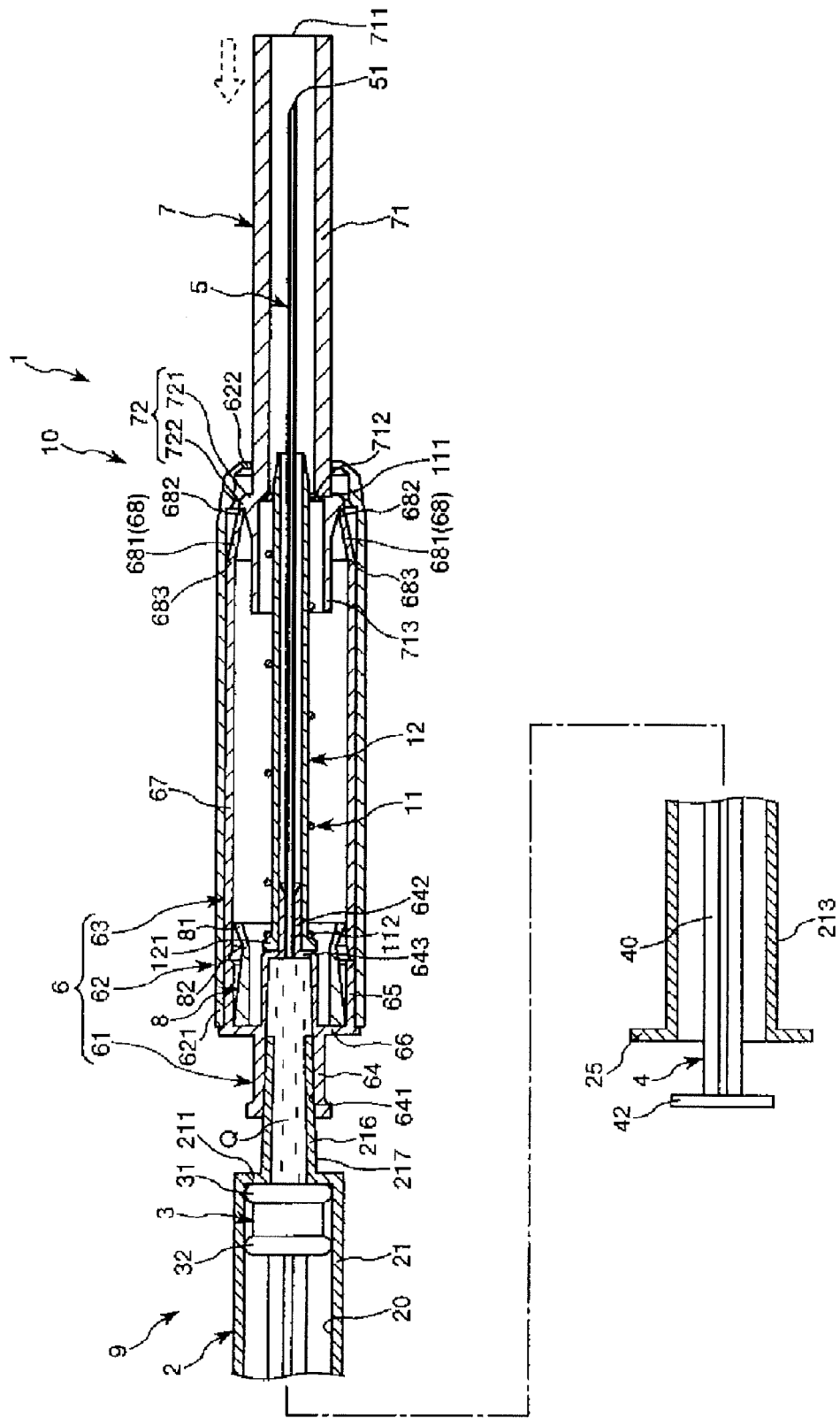
FIG. 8 is a longitudinal sectional view (a view corresponding to a section along line B-B of FIG. 1) for sequentially showing a state, during use of the first embodiment, of the medicinal liquid injection device (puncture needle assembly) according to the invention.

[5] When pressure toward the proximal side is exerted on the protector 7, starting from the state shown in FIG. 7, the protector 7 is about to move toward the second position. However, since the engagement section 722 of the protector 7 is engaged with the distal portions 682 of the small pieces 681, the protector 7 is prevented from moving toward the side of the second position (see FIG. 8). This makes it possible to securely prevent a situation in which an already used medicinal liquid injection device 1 might be reused by mistake, or in which the needle tube 5 might protrude to permit administration of a medicinal liquid Q into a living body through the needle tube 5.

[6] Further, in the case that use of the medicinal liquid injection device 1 is stopped during usage thereof, for example when the medicinal liquid injection device 1 (the protector 7) is separated from the living body surface 200 in the state shown in FIG. 5, the pressure exerted on the protector 7 from the living body surface 200 is released. As a result, in the same manner as mentioned above, the engagement preventing member 8 becomes disengaged from the proximal portion 713 of the protector body 71, and only the protector 7 is returned to the first position. When pressure toward the proximal side is exerted on the protector 7, starting from this state, the engagement section 722 of the rib 72 of the protector 7 comes into engagement with the distal portions 682 of the small pieces 681, whereby the protector 7 is inhibited from moving toward the side of the second position (see FIG. 9). This makes it possible to prevent a situation in which an already used medicinal liquid injection device 1 might be reused by mistake, or in which the needle tube 5 might protrude to enable administration of the medicinal liquid Q into a living body through the needle tube 5.

Thus, in the puncture needle assembly 10, in the cap-removed state, the restriction on the small pieces 681 by the presser ribs 145 of the first cap 14 is released, so that as mentioned above, the protector 7, which is located at the first position, is permitted to move to the second position. Then, when the protector 7 is moved from the first position to the second position, and then is returned again to the first position, the lock means operates as mentioned above, so as to restrict the protector 7 from moving again to the second position.

As shown in FIG. 1, on the inner peripheral portion 146 of the first cap 14, a plurality of (in the present embodiment, four) positioning ribs 148 are formed to project at positions on the proximal side relative to the presser ribs 145. The ribs 148 are arranged so as to correspond respectively to positions between two adjacent presser ribs 145, or at regular intervals along the circumferential direction of the first cap 14. Each of the ribs 148 is provided, on the proximal portion thereof, with a guide section 148*a*, which gradually decreases in width toward the proximal side.

In addition, on an outer peripheral portion of the outside member 62 of the main body section 6 of the puncture device 1, a plurality of (in the present embodiment, four) positioning ribs 624 are formed to project at positions on the proximal side relative to the small pieces 681 (slits 623). The positioning ribs 624 are arranged at regular intervals along the circumferential direction of the outside member 62, and the interval therebetween is set to be approximately equal to or slightly greater than the width of the positioning ribs 148 of the first cap 14. In addition, the positioning ribs 624 are arranged respectively corresponding to the slits 623. Further, each of the positioning ribs 624 is provided at a distal portion thereof with a guide section 624*a*, which gradually decreases in width toward the distal side.

In the case that the first cap 14 is mounted on the puncture device 13 to establish a cap-mounted state, as the first cap 14 is gradually fitted onto the puncture device 13, the guide sections 148*a* of the positioning ribs 148 of the first cap 14 are guided by the guide sections 624*a* of the positioning ribs 624 of the puncture device 13, which are closest to the positioning ribs 148. This ensures that the first cap 14 is rotated about its axis, whereby each of the positioning ribs 148 is located between two adjacent positioning ribs 624. As the fitting operation progresses further, the first cap 14 is positioned in such a manner that each of the presser ribs 145 enters into the slits 623 in the puncture device 13, so as to confront the small piece 681. This enables the small pieces 681 to be assuredly pressed by the presser ribs 145.

Thus, in the puncture needle assembly 10, the positioning ribs 148 of the first cap 14 and the positioning ribs 624 of the puncture device 13 function as a positioning means, by which positioning is carried out upon establishing the cap-mounted state, so as to cause the presser ribs 145 of the first cap 14 to confront the small pieces 681 of the puncture device 13.

Second Embodiment

Figure 10:
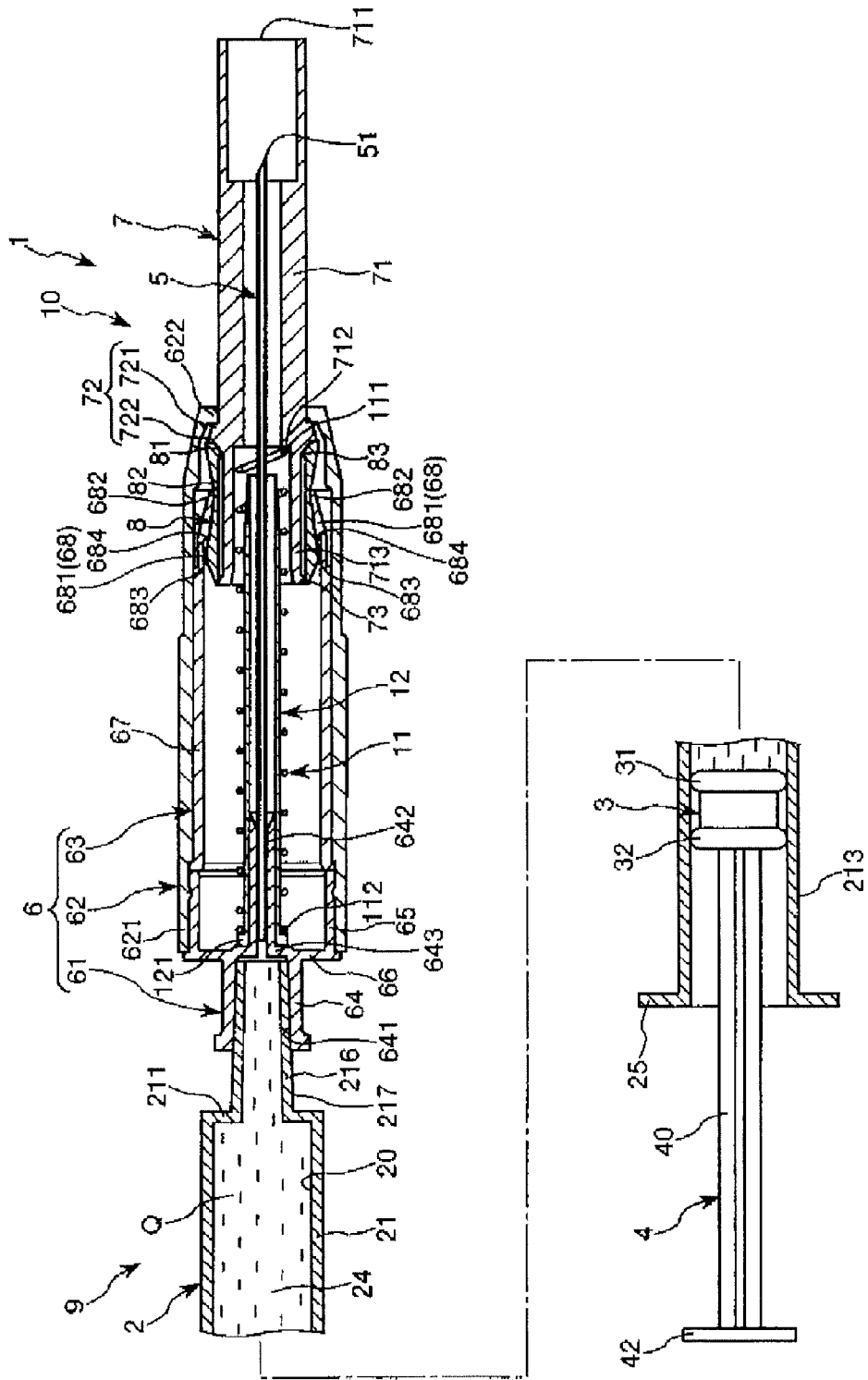
FIG. 10 is a longitudinal sectional view for sequentially showing a state, during use of a second embodiment, of a medicinal liquid injection device (puncture needle assembly) according to the present invention.
Figure 11:
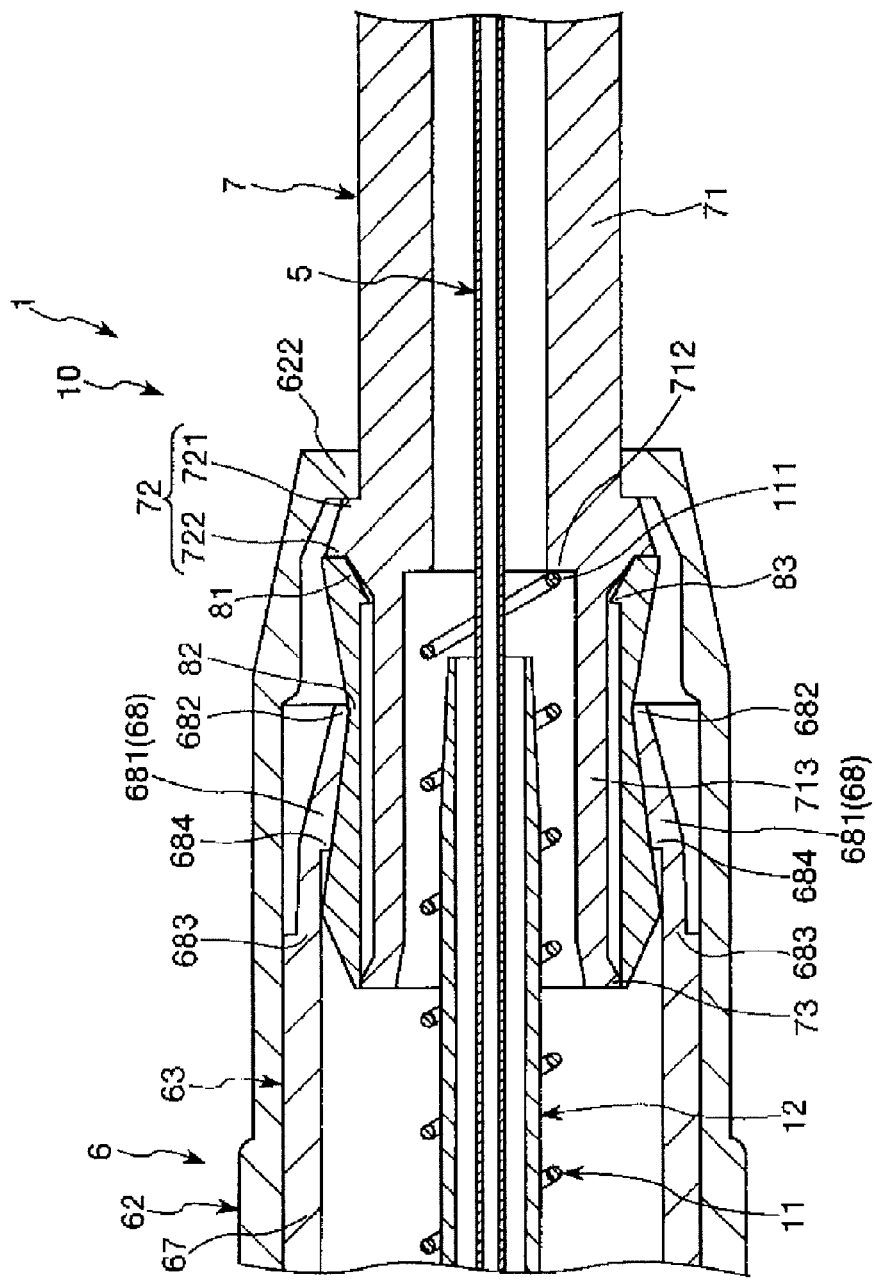
FIG. 11 is a longitudinal sectional view showing, in enlarged form, a major part of the medicinal liquid injection device shown in FIG. 10.
Figure 12:
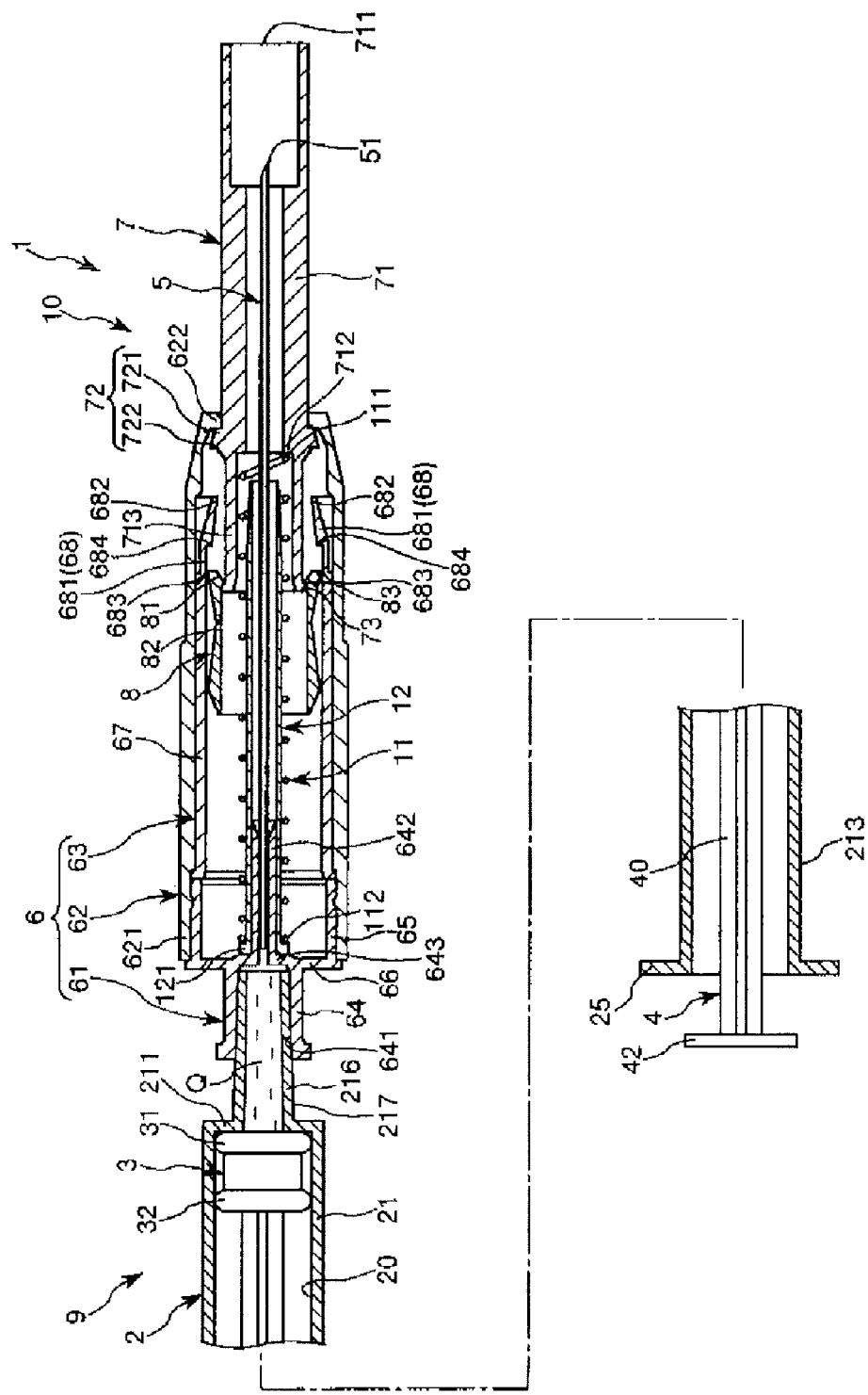
FIG. 12 is a longitudinal sectional view for sequentially showing a state during use of the medicinal liquid injection device shown in FIG. 10.
Figure 13:
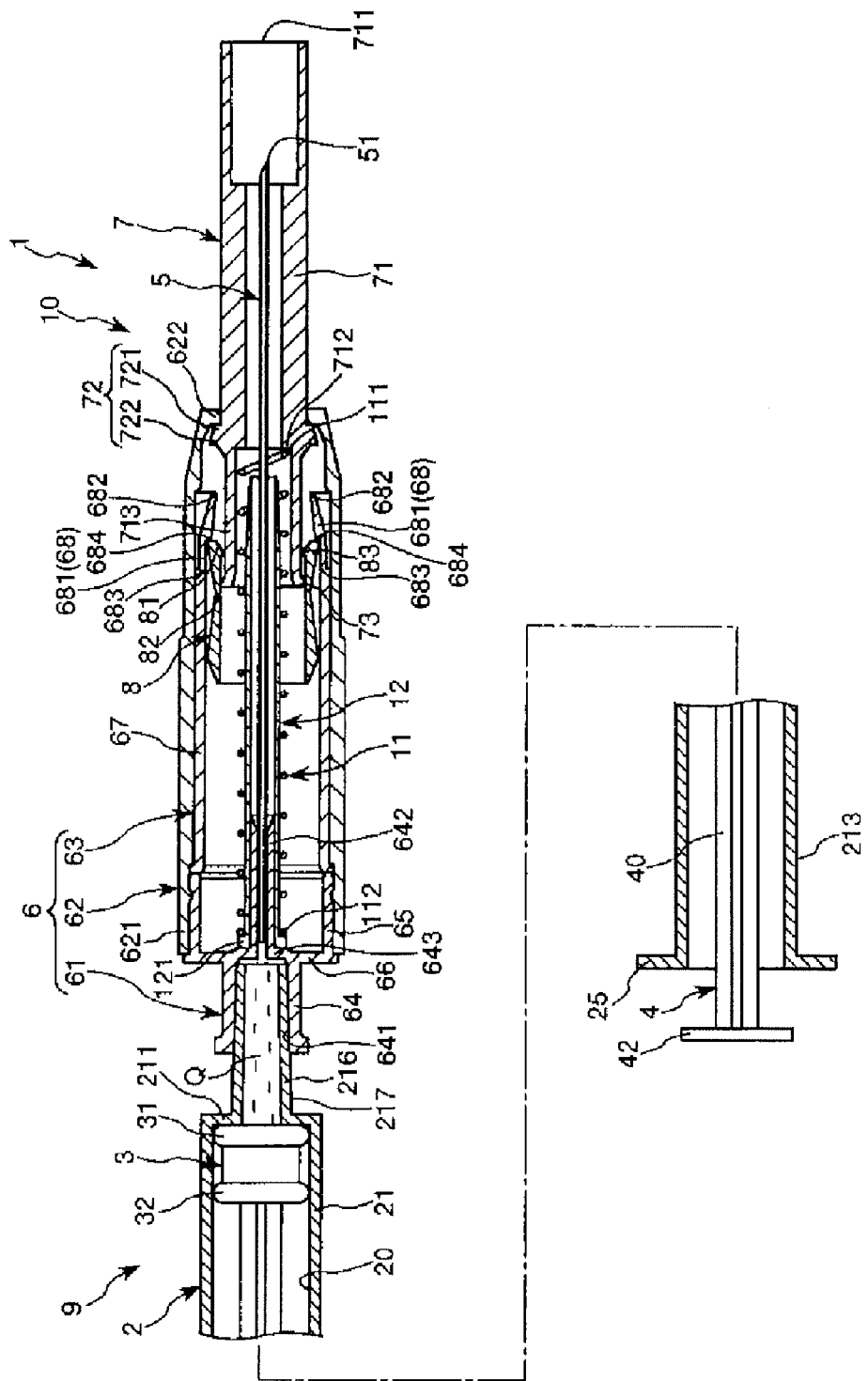
FIG. 13 is a longitudinal sectional view for sequentially showing a state during use of the medicinal liquid injection device shown in FIG. 10.
Figure 14:
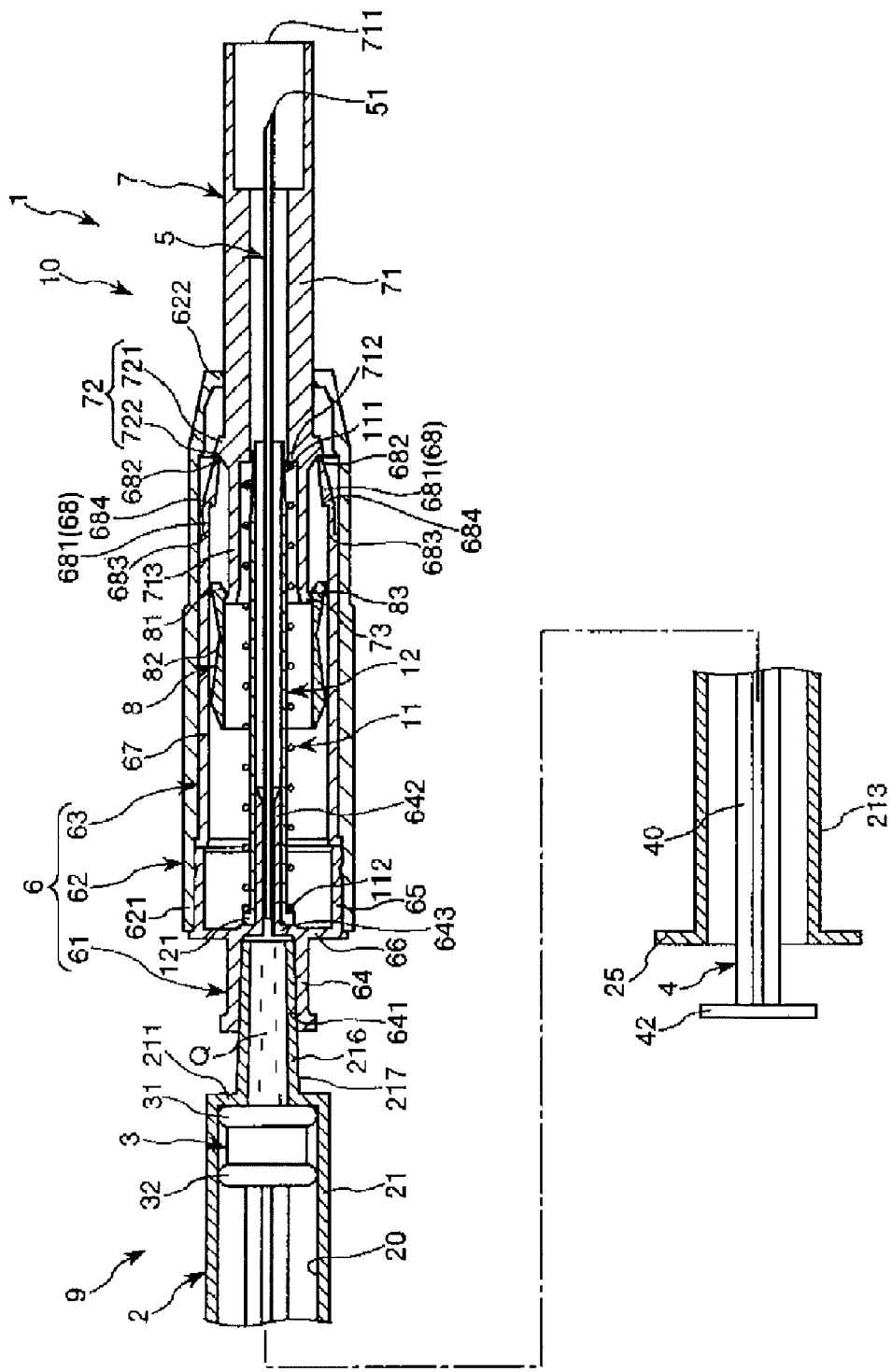
FIG. 14 is a longitudinal sectional view for sequentially showing a state during use of the medicinal liquid injection device shown in FIG. 10.

FIG. 10 is a longitudinal sectional view sequentially showing a state under use of a second embodiment of the medicinal liquid injection device (puncture needle assembly) according to the present invention. FIG. 11 is a longitudinal sectional view showing, in an enlarged form, a major part of the medicinal liquid injection device shown in FIG. 10. FIGS. 12 through 14 are longitudinal sectional views sequentially showing a state under use of the medicinal liquid injection device shown in FIG. 10.

Next, referring to these figures, the second embodiment of the puncture needle assembly and the medicinal liquid injection device according to the present invention will be described below. In the following descriptions, explanations shall be made mainly of differences from the above-described embodiment, and descriptions of the same items, which have already been discussed above, will be omitted.

In the puncture needle assembly 10 in the medicinal liquid injection device 1 according to the second embodiment shown in the figures, an engagement preventing member 8 is mounted on a proximal portion 713 of a protector body 71 of the protector 7, and more specifically, on an outer peripheral portion on the proximal side of an engagement section 722 of the protector body 71, in such a manner so as to be movable, but not engageable, in relation to the protector body 71.

As shown in FIGS. 10 and 11, a rib 83 is formed at an inner peripheral part of a distal portion 81 of the engagement preventing member 8. The rib 83 is formed to project in a ring-like shape along the circumferential direction of the engagement preventing member 8 over one entire circumference thereof.

On the other hand, on an outer peripheral part of a proximal portion 713 of the protector body 71, a rib 73 is formed, which can be engaged with the rib 83 of the engagement preventing member 8. The rib 73 is formed so as to project toward a side opposite to the needle tube 5 (outwardly), along the circumferential direction of the protector body 71 and over one entire circumference thereof. In other words, the rib 73 has a ring-like shape, the center of which lies along the center axis (axis) of the needle tube 5.

The ribs 73 and 83 constitute a disengagement preventing means, for preventing the engagement preventing member 8 from becoming disengaged from the proximal portion 713 of the protector body 71 (from the protector 7) at times when the protector 7 is moved from the second position to the first position.

In addition, the outside diameter of the outer peripheral part of the proximal portion of the engagement preventing member 8 gradually decreases along a direction from the distal side toward the proximal side thereof. This enables easy assembly of the puncture needle assembly 10.

Further, each of the small pieces 681 of the elastically deformable section 68 of an inside member 63 has a distal portion 682, which is inclined at an intermediate position thereof, from a base portion 683 toward the axis of the needle tube 5. In addition, at the intermediate position of each of the small pieces 681, a stepped part 684 is formed, with which a distal portion 81 of the engagement preventing member 8 can make contact. The stepped parts 684 of the small pieces 681 function as an assisting means, for assisting release of contact between the engagement preventing member 8 and the engagement section 722 (the rib 72), at a time when the protector 7 is moved from the second position to the first position.

When the protector 7 becomes spaced from the living body surface 200 after administration of a medicinal liquid Q, the protector 7 is pushed in the distal direction by the restoring force (biasing force) of the coil spring 11, so as to move toward and return to the first position, in the same manner as the first embodiment.

However, upon return of the medicinal liquid injection device 1 (the puncture needle assembly 10) to the first position, initially, the engagement preventing member 8 remains at the proximal portion of the main body section 6 due to frictional force acting between the hub 61 and the outer cylinder section 65, so that only the protector 7 moves toward the first position. Thus, contact between the engagement preventing member 8 and the rib 72 of the protector 7 is released. During this process, the rib 83 of the engagement preventing member 8 and the rib 73 of the protector 7 are engaged with each other, so that the engagement preventing member 8 is made to move toward the first position together with the protector 7. In other words, the engagement preventing member 8 is prevented from becoming disengaged from the proximal portion 713 of the protector body 71.

In addition, the protector 7 is moved from the second position to the first position, while the engagement preventing member 8 is mounted on the proximal portion 713 thereof. In this case, therefore, the portion of the protector body 71 on the distal side relative to the rib 72 is supported by a projection 622 of the outside member 62, and the proximal portion 713 is supported by a tubular section 67 of the inside member 63 through the engagement preventing member 8, thus enabling stable movement of the protector 7.

In this manner, the protector 7 is returned to the first position, whereas the engagement preventing member 8 remains on the proximal side of the small pieces 681, in a state of being mounted to the proximal portion 713 of the protector body 71, as shown in FIG. 12. This prevents the engagement preventing function of the engagement preventing member 8 from being exhibited again.

In a case where, for example, the engagement preventing member 8 is moved toward the first position together with the protector while in a state of making contact with the engagement section 722 of the engagement preventing member 8 upon return of the protector 7 to the first position, a distal portion 81 of the engagement preventing member 8 comes into contact with the stepped parts 684 of the small pieces 681, as shown in FIG. 13. This ensures that the engagement preventing member 8 is stopped in that position, and only the protector 7 moves toward the first position. Then, the protector 7 is returned to the first position, while the engagement preventing member 8 remains on the proximal side relative to the small pieces 681, in a state of being mounted to the proximal portion 713 of the protector body 71. This ensures that the engagement preventing function of the engagement preventing member 8 is not exhibited again.

In a case where pressure is exerted on the protector 7 in the proximal direction, starting from the state shown in FIGS. 12 and 13, the protector 7 attempts to move toward the second position. However, the engagement section 722 of the protector 7 engages with the distal portions 682 of the small pieces 681, whereby the protector 7 is prevented from moving toward the side of the second position (see FIG. 14). This makes it possible to securely prevent a situation in which an already used medicinal liquid injection device 1 is reused by mistake, or in which the needle tube 5 might protrude to enable administration of a medicinal liquid Q into a living body through the needle tube 5.

In addition, the protector 7, having returned to the first position, can securely be prevented from tottering, since a portion of the protector body 71, which is on the distal side relative to the rib 72, is supported by the projection 622 of the outside member 62, whereas the proximal portion 713 thereof is supported, via the engagement preventing member 8, by the tubular section 67 of the inside member 63.

Incidentally, in the present embodiment, similar to the first embodiment described above, the lock release means is securely prevented, by the presser ribs 145 of the first cap 14, from operating in an unintentional manner in the cap-mounted state. This makes it possible to prevent a situation in which the protector 7, which is located in the first position, might inadvertently be moved to the second position and returned again to the first position, in which the lock means could possibly be operated.

Third Embodiment

Figure 15:
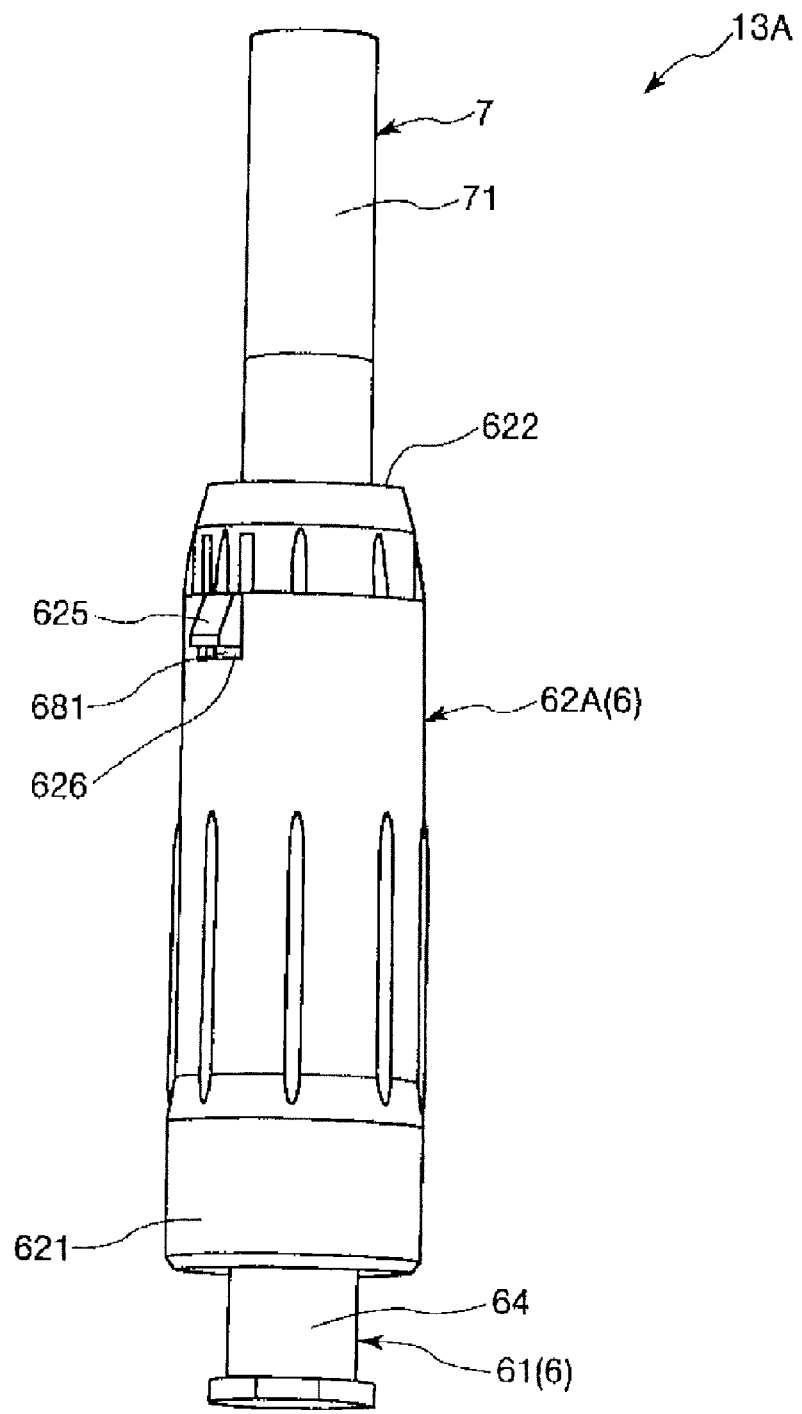
FIG. 15 is a perspective view showing a cap-removed state of a third embodiment of the puncture needle assembly according to the present invention.
Figure 16:
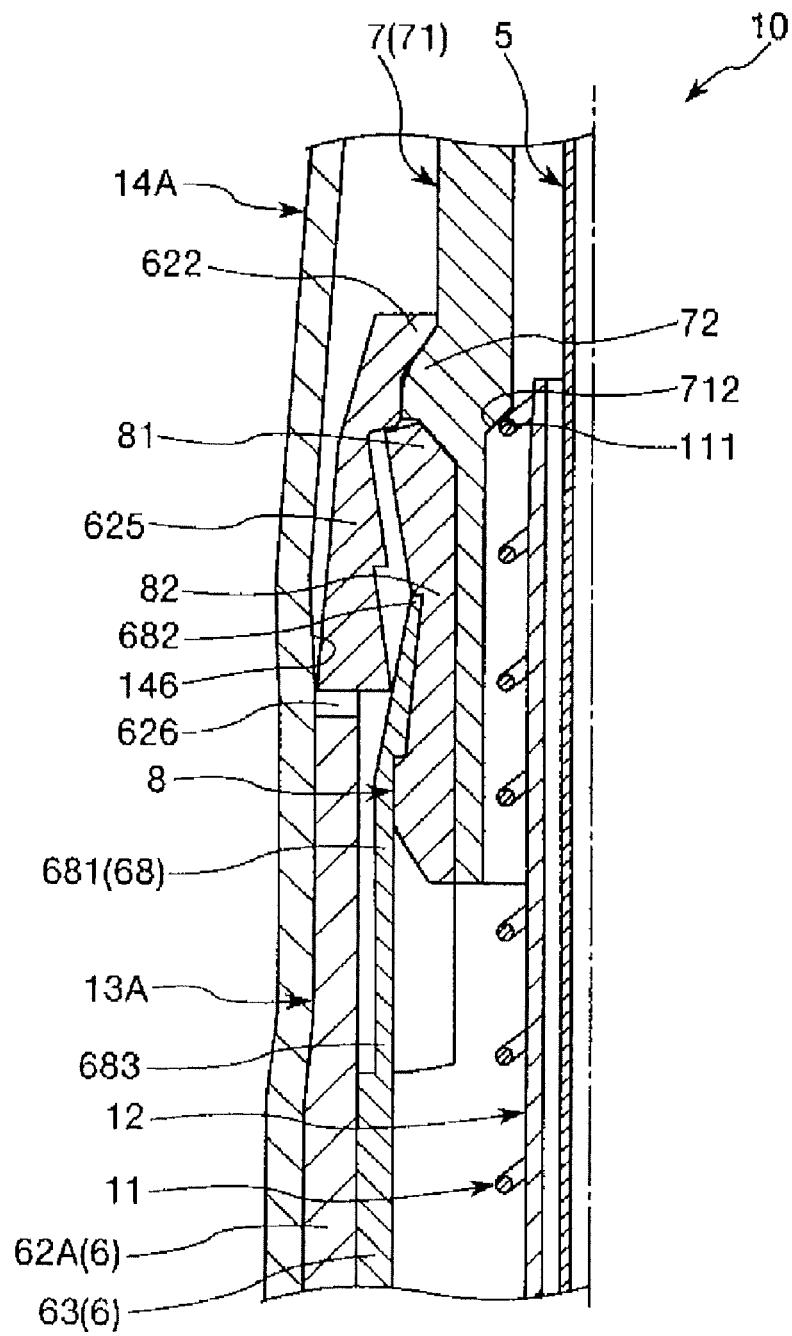
FIG. 16 is a longitudinal sectional view showing a major part of the puncture needle assembly shown in FIG. 15.

FIG. 15 is a perspective view showing a cap-removed state of a third embodiment of the puncture needle assembly according to the present invention, whereas FIG. 16 is a longitudinal sectional view showing a principal portion of the puncture needle assembly shown in FIG. 15.

Next, with reference to the figures, a third embodiment of the puncture needle assembly and the medicinal liquid injection device according to the present invention will be described. In the following descriptions, explanations shall be made concerning differences from the above-described embodiments, and detailed descriptions of items that are the same as the above shall be omitted.

The embodiment is the same as the above-described first embodiment, except for differences in the configuration of an outside member of the main body section of a puncture device.

In the puncture device 13A shown in FIGS. 15 and 16, an outside member 62A of a main body section 6 is provided with a plurality of presser pieces 625, which are capable of pressing small pieces 681 of an inside member 63. Each of the presser pieces 625 makes up a part, which is surrounded by a slit 626 formed in a roughly angular U-shape, so as to penetrate through the tube wall of a tubular outside member 62A. This permits each of the presser pieces 625 to undergo elastic deformation (flexure). In addition, the presser pieces 625 are arranged on the outer peripheral side of the small pieces 681 of the inside member 63.

As shown in FIG. 16, in a cap-mounted state, each of the presser pieces 625 is pressed by a part of an inner peripheral portion 146 of a first cap 14A. In addition, the small pieces 681 are pressed through the presser pieces 625 toward the inner side, whereby distal portions 682 thereof become engaged with a contact section 82 of the engagement preventing member 8. This ensures that even when the puncture needle assembly 10 in the cap-mounted state is dropped by mistake, for example, a situation in which impact of the dropping could cause the protector 7 located in the first position to move beyond the small pieces 681 of the main body section 6 of a puncture device 13 together with the engagement preventing member 8, and to move to the second position as mentioned above, can be restricted (prevented). As a result, a situation in which the protector 7 located in the first position might inadvertently be moved to the second position and returned again to the first position, in which the lock means might be operated, can securely be prevented.

Incidentally, in the present embodiment, the first cap 14A differs from that of the first embodiment, in that the presser ribs 145 are omitted, and a part of an inner peripheral portion 146 thereof functions in a similar manner to the presser ribs 145.

Fourth Embodiment

Figure 17:
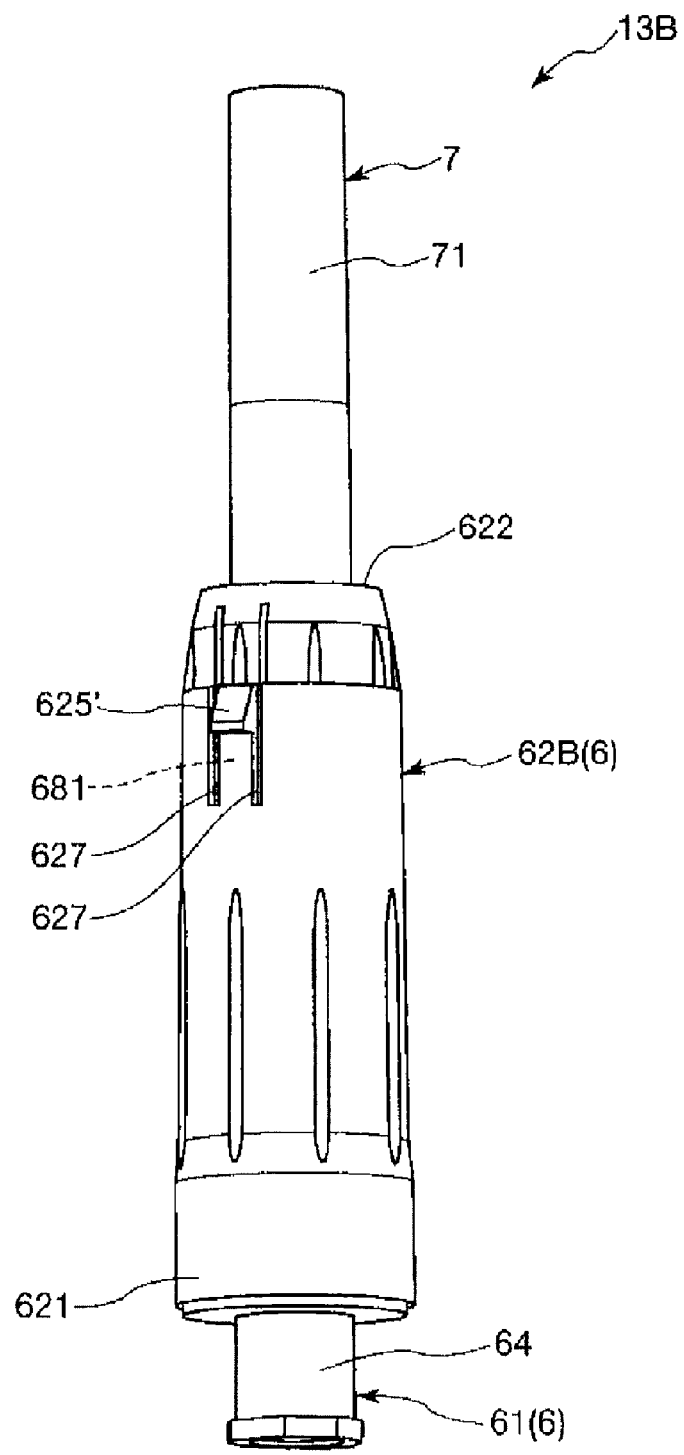
FIG. 17 is a perspective view showing a cap-removed state of a fourth embodiment of a puncture needle assembly according to the present invention.

FIG. 17 is a perspective view showing a cap-removed state of a fourth embodiment of the puncture needle assembly according to the present invention.

The fourth embodiment of the puncture needle assembly and the medicinal liquid injection device according to the present invention will be described below with reference to the drawings. Descriptions will be made focusing mainly on differences from the above-described embodiments, and descriptions of the same items will be omitted.

The present embodiment is the same as the third embodiment above, except for differences in the configuration of the presser pieces.

In the puncture device 13B shown in FIG. 17, an outside member 62B of the main body section 6 is provided with a plurality of presser pieces 625', which are capable of pressing small pieces 681 of an inside member 63. Each of the presser pieces 625' forms a part located between two slits 627, which penetrates through a tube wall of a tubular outside member 62A, in a rectilinear shape along the longitudinal direction thereof. Such a feature permits elastic deformation of each of the presser pieces 625'. In addition, the presser pieces 625' are arranged along the outer peripheral side of the small pieces 681 of the inside member 63.

Also, in a cap-mounted state of the present embodiment, the small pieces 681 are pressed toward the inner side through the presser pieces 625, whereby distal portions 682 thereof engage with a contact section 82 of the engagement preventing member 8, similar to the third embodiment above.

While the puncture needle assembly and the medicinal liquid injection device according to the present invention have been described above with reference to the embodiments shown in the drawings, the invention is not limited to the above embodiments. Parts or elements constituting the puncture needle assembly and the medicinal liquid injection device may be replaced by arbitrary configurations, which can exhibit the same or similar functions to those mentioned above. Arbitrary structures may also be added thereto.

In addition, either of the puncture needle assembly or the medicinal liquid injection device according to the present invention may be a combination of any arbitrary two or more configurations (characteristic features) of the above-described embodiments.

Further, in the present invention, the puncture needle assembly is not limited to being used as an injection needle, and may, for example, be used as a needle for drawing blood.

INDUSTRIAL APPLICABILITY

The puncture needle assembly according to the present invention includes a puncture device, which is provided with a needle tube having a sharp needlepoint at a distal end thereof, and also with a protector, which is supported relative to the needle tube so as to be movable in the axial direction of the needle tube between a first position, at which the protector covers at least the needlepoint of the needle tube, and a second position, at which the protector exposes the needlepoint and which is located on the proximal side relative to the first position. The puncture needle assembly further includes a cap, which is removably mounted on the puncture device, lock means which, when the protector is at the first position, is capable of maintaining the position of the protector, and lock release means which, when the protector moves from the first position to the second position, enables the protector to move by releasing a locked state maintained by the lock means. The cap has a prevention section, which prevents the lock means from becoming unlocked in a cap-mounted state, in which the cap is mounted on the puncture device with the protector located at the first position. Therefore, in the cap-mounted state, the prevention section of the cap securely prevents the lock release means from being operated inadvertently. Consequently, the lock means can securely be prevented from operating if the protector, when located at the first position, is moved inadvertently to the second position and then returned again to the first position.

In addition, even if the protector, which has moved from the first position to the second position and then is returned again to the first position, attempts to move further toward the second position, movement of the protector is restricted. More specifically, since the lock means is in operation, movement of the protector toward the second position is inhibited. This ensures that the needlepoint of the needle tube can securely be prevented from becoming inadvertently exposed from the protector, and thus erroneous puncturing with the needlepoint is prevented more assuredly.

Accordingly, the puncture needle assembly of the present invention has industrial applicability.

The invention claimed is:

1. A puncture needle assembly comprising:
   a puncture device, which is provided with a needle tube having a sharp needlepoint at a distal end thereof, and a protector, which is supported relative to the needle tube so as to be movable in an axial direction of the needle tube between a first position, at which the protector covers at least the needlepoint of the needle tube, and a second position, at which the protector exposes the needlepoint and is located on a proximal side relative to the first position;
   a cap removably mounted on the puncture device;
   lock means which, when the protector is at the first position, is capable of maintaining the position of the protector; and
   lock release means which, when the protector moves from the first position to the second position, enables the protector to move by releasing a locked state maintained by the lock means;
   wherein:
   the cap has a prevention section which, in a cap-mounted state in which the cap is mounted on the puncture device with the protector located at the first position, prevents the lock means from becoming unlocked;
   the puncture device has a main body section comprising an elastically deformable section;
   the protector has an engaging section capable of engaging with the elastically deformable section which has not elastically deformed outwardly when the protector is located at the first position;
   the lock means is composed of the elastically deformable section and the engaging section;
   the lock release means is composed of an engagement preventing member, wherein when the protector moves from the first position toward the second position, the engagement preventing member comes into contact with the engaging section to move along with the protector and the elastically deformable section elastically deforms outwardly, and whereby the engagement preventing member exhibits an engagement preventing function, by which the engaging section is permitted to pass by the elastically deformable section without coming into engagement with the elastically deformable section; and
   in the cap-mounted state, the prevention section pushes the elastically deformable section toward the engagement preventing member, so as to bring the elastically deformable section into close contact with an outer peripheral portion of the engagement preventing member, thereby preventing the engagement preventing member from passing by the elastically deformable section.

2. The puncture needle assembly according to claim 1, wherein:
   the lock release means is prevented from operating in the cap-mounted state; and
   the lock release means is permitted to operate in a cap-removed state.

3. A medicinal liquid injection device comprising the puncture needle assembly according to claim 2, and further comprising:
   a vessel, which is prefilled with a medicinal liquid, on which the puncture device of the puncture needle assembly is mounted, and which communicates with the needle tube in the mounted state.

4. The puncture needle assembly according to claim 1, comprising:
biasing means, which biases the protector in a direction away from the second position and toward the first position,
wherein, when the protector is pushed to move from the first position to the second position against a biasing force of the biasing means and then pushing thereof is released, the protector is biased by the biasing force of the biasing means to move to the first position; and
wherein, when the protector at the first position thereafter attempts to move toward the second position, the lock means operates to prevent movement of the protector toward the side of the second position.

5. A medicinal liquid injection device comprising the puncture needle assembly according to claim 4, and further comprising:
a vessel, which is prefilled with a medicinal liquid, on which the puncture device of the puncture needle assembly is mounted, and which communicates with the needle tube in the mounted state.

6. The puncture needle assembly according to claim 1, comprising:
positioning means which, when the cap-mounted state is established, performs positioning such that the prevention section confronts the elastically deformable section.

7. A medicinal liquid injection device comprising the puncture needle assembly according to claim 6, and further comprising:
a vessel, which is prefilled with a medicinal liquid, on which the puncture device of the puncture needle assembly is mounted, and which communicates with the needle tube in the mounted state.

8. The puncture needle assembly according to claim 1, wherein the prevention section constitutes a part of an inner peripheral portion of the cap.

9. A medicinal liquid injection device comprising the puncture needle assembly according to claim 8, and further comprising:
a vessel, which is prefilled with a medicinal liquid, on which the puncture device of the puncture needle assembly is mounted, and which communicates with the needle tube in the mounted state.

10. A medicinal liquid injection device comprising the puncture needle assembly according to claim 1, and further comprising:
a vessel, which is prefilled with a medicinal liquid, on which the puncture device of the puncture needle assembly is mounted, and which communicates with the needle tube in the mounted state.

11. A puncture needle assembly comprising:
a puncture device, which is provided with a needle tube having a sharp needlepoint at a distal end thereof, and a protector, which is supported relative to the needle tube so as to be movable in an axial direction of the needle tube between a first position, at which the protector covers at least the needlepoint of the needle tube, and a second position, at which the protector exposes the needlepoint and is located on a proximal side relative to the first position;
a cap removably mounted on the puncture device;
lock means which, when the protector is at the first position, is capable of maintaining the position of the protector; and
lock release means which, when the protector moves from the first position to the second position, enables the protector to move by releasing a locked state maintained by the lock means;
wherein:
the cap has a prevention section which, in a cap-mounted state in which the cap is mounted on the puncture device with the protector located at the first position, prevents the lock means from becoming unlocked;
the puncture device has a main body section comprising a tubular body section in which a portion of the needle tube is inserted, a hub to which a proximal portion of the needle tube is fixed and which is disposed at a proximal portion of the tubular body section, and an elastically deformable section provided on a distal side relative to the proximal portion of the tubular body section;
the protector is supported on the main body section and has an engaging section capable of engaging with the elastically deformable section when the protector is located at the first position;
the lock means is composed of the elastically deformable section and the engaging section;
the lock release means is composed of an engagement preventing member which, when the protector moves from the first position toward the second position, comes into contact with the engaging section and thereby exhibits an engagement preventing function, by which the engaging section is permitted to pass by the elastically deformable section without coming into engagement with the elastically deformable section;
the engagement preventing member is mounted removably on the protector;
the elastically deformable section is located on the outer peripheral side of the engagement preventing member in a state in which the engagement preventing member is mounted on the protector when the protector is located at the first position; and
in the cap-mounted state, the prevention section pushes the elastically deformable section toward the engagement preventing member, so as to bring the elastically deformable section into close contact with an outer peripheral portion of the engagement preventing member, thereby preventing the engagement preventing member from passing by the elastically deformable section.

12. A medicinal liquid injection device comprising the puncture needle assembly according to claim 11, and further comprising:
a vessel, which is prefilled with a medicinal liquid, on which the puncture device of the puncture needle assembly is mounted, and which communicates with the needle tube in the mounted state.

13. A puncture needle assembly comprising:
a puncture device, which is provided with a needle tube having a sharp needlepoint at a distal end thereof, and a protector, which is supported relative to the needle tube so as to be movable in an axial direction of the needle tube between a first position, at which the protector covers at least the needlepoint of the needle tube, and a second position, at which the protector exposes the needlepoint and is located on a proximal side relative to the first position;
a cap removably mounted on the puncture device;
lock means which, when the protector is at the first position, is capable of maintaining the position of the protector; and lock release means which, when the protector moves from the first position to the second position, enables the protector to move by releasing a locked state maintained by the lock means;

wherein:

the cap has a prevention section which, in a cap-mounted state in which the cap is mounted on the puncture device with the protector located at the first position, prevents the lock means from becoming unlocked;

the puncture device has a main body section comprising a tubular body section in which a portion of the needle tube is inserted, a hub to which a proximal portion of the needle tube is fixed and which is disposed at a proximal portion of the tubular body section, and an elastically deformable section provided on a distal side relative to the proximal portion of the tubular body section;

the protector is supported on the main body section and has an engaging section capable of engaging with the elastically deformable section when the protector is located at the first position;

the lock means is composed of the elastically deformable section and the engaging section;

the lock release means is composed of an engagement preventing member which, when the protector moves from the first position toward the second position, comes into contact with the engaging section and thereby exhibits an engagement preventing function, by which the engaging section is permitted to pass by the elastically deformable section without coming into engagement with the elastically deformable section;

the engagement preventing member is mounted removably on the protector;

the main body section has a pushing piece, which is disposed on the outer peripheral side of the elastically deformable section and pushes the elastically deformable section, and the elastically deformable section is located on the outer peripheral side of the engagement preventing member in a state in which the engagement preventing member is mounted on the protector when the protector is located at the first position; and in the cap-mounted state, the preventing section pushes the elastically deformable section through the pushing piece and toward the engagement preventing member, so as to bring the elastically deformable section into close contact with an outer peripheral portion of the engagement preventing member, thereby preventing the engagement preventing member from passing by the elastically deformable section.

14. A medicinal liquid injection device comprising the puncture needle assembly according to claim 13, and further comprising:

a vessel, which is prefilled with a medicinal liquid, on which the puncture device of the puncture needle assembly is mounted, and which communicates with the needle tube in the mounted state.

\* \* \* \* \*